US006812290B2

United States Patent
Goto et al.

(10) Patent No.: US 6,812,290 B2
(45) Date of Patent: Nov. 2, 2004

(54) POLYARYLENE COPOLYMERS AND PROTON-CONDUCTIVE MEMBRANE

(75) Inventors: Kohei Goto, Tsukuba (JP); Yoshitaka Yamakawa, Tsukuba (JP); Mayumi Kakuta, Tsukuba (JP); Igor Rozhanskii, Tsukuba (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 10/303,821

(22) Filed: Nov. 26, 2002

(65) Prior Publication Data

US 2003/0195301 A1 Oct. 16, 2003

Related U.S. Application Data

(63) Continuation-in-part of application No. 09/818,847, filed on Mar. 28, 2001, now Pat. No. 6,555,626.

(30) Foreign Application Priority Data

Mar. 29, 2000 (JP) .................................... P. 2000-091259
May 24, 2000 (JP) .................................... P. 2000-153047

(51) Int. Cl.[7] .............................. C08F 8/36; C08G 65/38

(52) U.S. Cl. ..................... 525/242; 525/288; 525/291; 525/293; 528/86; 528/171; 528/205; 528/219; 528/211; 528/373

(58) Field of Search ................................. 525/242, 288, 525/291, 293; 528/86, 171, 205, 219, 211, 373

(56) References Cited

U.S. PATENT DOCUMENTS

| | | | |
|---|---|---|---|
| 6,084,053 A | 7/2000 | Matsubara et al. | |
| 6,300,465 B1 | 10/2001 | Akiike et al. | |
| 6,555,626 B2 * | 4/2003 | Goto et al. | ................. 525/242 |

* cited by examiner

Primary Examiner—Duc Truong
(74) Attorney, Agent, or Firm—Oblon, Spivak, McClelland, Maier & Neustadt, P.C.

(57) ABSTRACT

A polyarylene copolymer which comprises (A) aromatic compound units having a main chain containing one or more electron-withdrawing groups therein and (B) aromatic compound units having a main chain containing no electron-withdrawing groups therein, and a proton-conductive membrane comprising the polyarylene copolymer having sulfonic acid groups.

12 Claims, 13 Drawing Sheets

POLYARYLENE COPOLYMERS AND PROTON-CONDUCTIVE MEMBRANE

CROSS-REFERENCE TO THE RELATED APPLICATION

This application is a continuation-in-part application of application Ser. No. 09/818,847 filed Mar. 28, 2001, now U.S. Pat. No. 6,555,626, entitled "POLYARYLENE COPOLYMERS AND PROTON-CONDUCTIVE MEMBRANE".

FIELD OF THE INVENTION

The present invention relates to polyarylene copolymers. More particularly, the invention relates to a polyarylene copolymers useful as a proton-conductive membrane utilizable in applications such as electrolytes for primary batteries, electrolytes for secondary batteries, solid polymer electrolytes for fuel cells, display elements, various sensors, signal-transmitting media, solid capacitors, and ion-exchange membranes. The invention further relates to a proton-conductive membrane formed from the copolymer.

DESCRIPTION OF THE RELATED ART

Electrolytes are usually used as (aqueous) solutions in many cases. In recent years, however, there is a growing tendency to replace such aqueous soluble-form electrolytes with solid electrolytes. The first reason for this is the easiness of processing in applications of solid electrolytes to, e.g., the electrical/electronic materials mentioned above. The second reason is the trend toward reduction in weight, thickness, length and size, and toward energy saving.

Conventional proton-conductive materials include both inorganic materials and organic materials. Examples of the inorganic materials include uranyl phosphates which form hydrate. However, these inorganic compounds are insufficient in interfacial contact to pose many problems concerning the formation of a conductive layer on a substrate or electrode.

On the other hand, examples of the organic compounds include organic polymers such as polymers belonging to the so-called cation-exchange resins, e.g., sulfonated vinyl polymers such as sulfonated polystyrene (co)polymers with perfluoroalkylsulfonic acid represented by Nafion (manufactured by E.I. du Pont de Nemours & Co., Inc.), and perfluoroalkylcarboxylic acid polymers, and polymers prepared with incorporating sulfonic acid groups or phosphonic acid groups into heat-resistant polymers such as polybenzimidazole and poly(ether-ether-ketone)s [see *Polymer Preprints*, Japan, Vol.42, No.7, pp.2490-2492 (1993); *Polymer Preprints*, Japan, Vol.43, No.3, pp.735-736 (1994); and *Polymer Preprints*, Japan, Vol.42, No.3, p.730 (1993)].

Although these organic polymers are usually used in the form of a membrane, a conductive membrane thereof can be bonded to an electrode while taking advantage of the solvent-soluble or thermoplasticity thereof. However, many of those organic polymers have the following problems besides being still insufficient in proton conductivity. The organic polymers deteriorate in mechanical properties and durability or in proton conductivity at elevated temperatures (100° C. or higher), and the proton conductivity thereof highly depends on humidity conditions. Adhesion to the electrode is not fully satisfactory. Furthermore, the conductive membrane swells excessively during operation due to the hydrophilic polymer structure, and this swelling leads to a decrease in strength properties or a deformation. Consequently, application of those organic polymers to the aforementioned electrical/electronic materials and the like pose various problems.

U.S. Pat. No. 5,403,675 proposes a solid polymer electrolyte comprising a sulfonated rigid polyphenylene. This polymer is produced from a polymer comprising a phenylene chain obtained by polymerizing an aromatic compound (the polymer structure is described in column 9 in the specification) by reacting the phenylene polymer as the main component with a sulfonating agent to incorporate sulfonic acid groups thereinto. However, the incorporation of a large amount of sulfonic acid groups results in a sulfonated polymer having considerably impaired mechanical strength properties although proton conductivity improves with the increasing amount of sulfonic acid groups incorporated. It is therefore necessary to regulate the concentration of sulfonic acid groups to a proper value which enables the sulfonated polymer to retain intact excellent mechanical properties and have proton conductivity. Virtually, however, sulfonation of this polymer is apt to proceed excessively and it is exceedingly difficult to properly regulate the amount of sulfonic groups incorporated.

SUMMARY OF THE INVENTION

The invention has been achieved in view of the conventional technical problems.

One object of the invention is to provide polyarylene copolymers which can be sulfonated while being easily regulated with respect to the upper limit of sulfonic acid group incorporation amount so as not to impair mechanical properties and thus gives a sulfonated polymer which has high proton conductivity in a wide temperature range, has excellent mechanical strength, is reduced in swelling in hot water, and gives a proton-conductive membrane having excellent durability.

Another object of the invention is to provide a proton-conductive membrane formed from the copolymer.

The invention provides polyarylene copolymers which comprise (A) aromatic compound units having a main chain containing one or more electron-withdrawing groups and one or more ether bonds therein (hereinafter referred to also as "units (A)") and (B) aromatic compound units having a main chain containing no electron-withdrawing groups therein.

The electron-withdrawing groups preferably are divalent groups which are at least one member selected from the group consisting of —CO—, —CONH—, —(CF$_2$)$_p$— (wherein p is an integer of 1 to 10), —C(CF$_3$)$_2$—, —COO—, —SO—, and —SO$_2$—.

The polyarylene copolymer of the invention preferably are polyarylene copolymers having sulfonic acid groups (hereinafter referred to also as "sulfonic acid-containing copolymer" or "sulfonated polymer").

The invention further provides proton-conductive membranes comprising the sulfonic acid-containing copolymers.

DETAILED DESCRIPTION OF THE INVENTION

Figure 1:
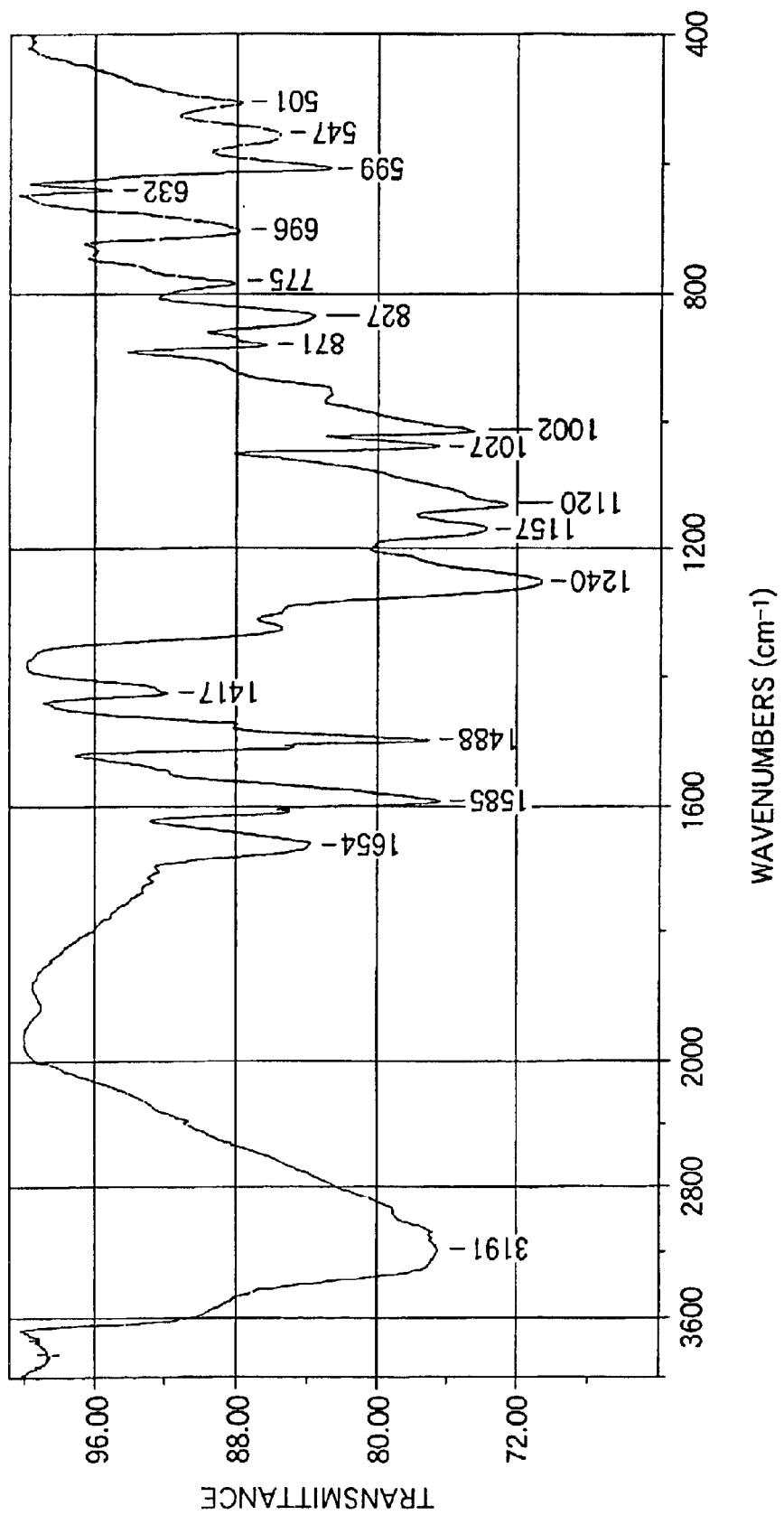
FIG. 1 is an IR chart of the sulfonated polymer obtained in Example 1.

The polyarylene copolymer of the invention comprises (A) aromatic compound units having a main chain containing one or more electron-withdrawing groups therein and (B) aromatic compound units having a main chain containing no electron-withdrawing groups therein.

Examples of units (A) include aromatic compound units represented by the following general formula (1), while examples of units (B) include aromatic compound units represented by at least one of the following formulae (2) to (4).

The term "electron-withdrawing group" as used herein means a group having a Hammett's substituent constant of 0.06 or larger or 0.01 or larger when located in a meta position or the para position, respectively, in the phenyl group.

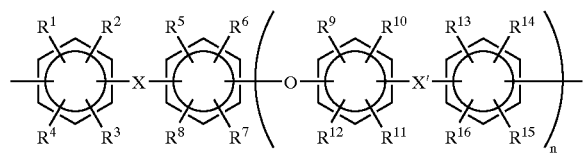

(1)

wherein X and X' may be the same or different and each represents at least one divalent electron-withdrawing group selected from the group consisting of —CO—, —CONH—, —(CF$_2$)$_p$— (wherein p is an integer of 1 to 10), —C(CF$_3$)$_2$—, —COO—, —SO—, and —SO$_2$—; R$^1$ to R$^{16}$ may be the same or different and each represents a hydrogen atom, a halogen atom, an alkyl group, a halogenoalkyl group, an allyl group, or an aryl group; and n is a number of 0 or 1.

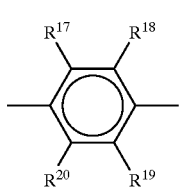

(2)

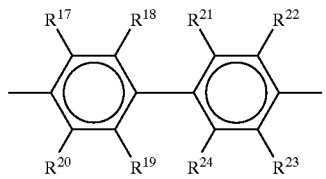

(3)

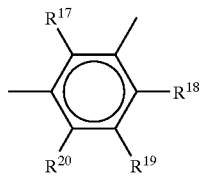

(4)

in general formulae (2) to (4), R$^{17}$ to R$^{24}$ may be the same or different and each represents a hydrogen atom, an alkyl group, a halogen atom, a halogenoalkyl group, an aryl group, or a group represented by the formula

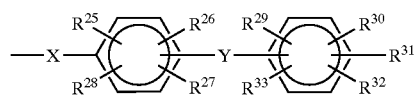

wherein X represents an electron-withdrawing divalent group; Y represents an electron-donating divalent group; and R$^{25}$ to R$^{33}$ each represents a hydrogen atom, an alkyl group, a halogen atom, a halogenoalkyl group, or an aryl group.

Specific examples of R$^1$ to R$^{16}$ in general formula (1) are as follows. Examples of the halogen atom include fluorine atom. Examples of the alkyl group include methyl and ethyl. Examples of the halogenoalkyl group include trifluoromethyl and pentafluoroethyl. Examples of the allyl group include propenyl. Examples of the aryl group include phenyl and pentafluorophenyl.

In general formulae (2) to (4), R$^{17}$ to R$^{24}$ may be the same or different and represent a hydrogen atom, an alkyl group, a halogen atom, a halogenoalkyl group, or a monovalent organic group containing one or more functional groups which do not inhibit a polyarylene-polymerization reaction.

Examples of the alkyl group represented by R$^{17}$ to R$^{24}$ include methyl, ethyl, propyl, butyl, pentyl, and hexyl.

Examples of the halogen atom include chlorine, bromine, and iodine atoms. Examples of the halogenoalkyl group include trifluoromethyl, perfluoroethyl, perfluoropropyl, perfluorobutyl, perfluoropentyl, and perfluorohexyl.

In the formula

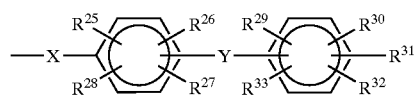

examples of the electron-withdrawing group represented by X include the same electron-donating groups enumerated above with regard to general formula (I), and examples of the electron-donating group represented by Y include —O— and —S—. Specific examples of the group represented by the formula include 4-phenoxyphenylcarbonyl.

In the polyarylene copolymers of the invention, the proportion of units (A) is 60 mol % or less, preferably from 60 to 0.01 mol %, more preferably from 40 to 0.01 mol %.

If the proportion of units (A) exceeds 60 mol %, not only the polyarylene copolymers obtained have poor solubility leaded processability, but also sulfonic acid groups cannot be incorporated after polymerization in an amount sufficient to enable the polymer to have proton conductivity.

The polyarylene copolymers of the invention comprise repeating structural units represented by general formula (1) given above [units (A)] and repeating structural units represented by at least one of general formulae (2) to (4) given above [units (B)].

The sulfonic acid-containing copolymers are, for example, polymers obtained by copolymerizing a monomer corresponding to general formula (1) with one or more monomers corresponding to at least one of general formulae (2) to (4) in the presence of a catalyst comprising a transition metal compound and sulfonating the resultant copolymers with a sulfonating agent.

The polyarylene copolymers of the invention are prepared, for example, with polymerizing an aromatic compound which has a main chain containing one or more electron-withdrawing groups and one or more ether bonds therein and is represented by the following general formula (1)' (hereinafter referred to also as "monomer (A)") with at least one aromatic compound represented by at least one of the following general formulae (2)' to (4)' (hereinafter referred to also as "monomer (B)") in a solvent in the presence of a catalyst comprising a transition metal compound.

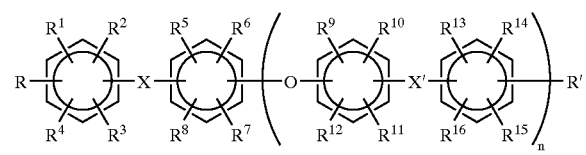
(1)'

In general formula (1)' given above, X, X', $R^1$ to $R^{16}$, and n are the same as in general formula (1); and R and R' may be the same or different and each represents a halogen atom other than fluorine or a group represented by —$OSO_2Z$ (wherein Z represents an alkyl group, a halogenoalkyl group, or an aryl group).

Examples of the halogen atom represented by R or R' in general formula (1)' include chlorine, bromine, and iodine atoms. In the group —$OSO_2Z$ in general formula (1)', examples of the alkyl group represented by Z include methyl and ethyl, examples of the halogenoalkyl group represented thereby include trifluoromethyl, and examples group represented thereby include phenyl and p-tolyl.

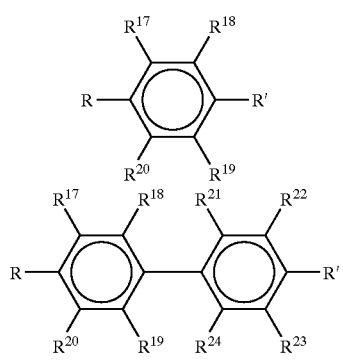

-continued

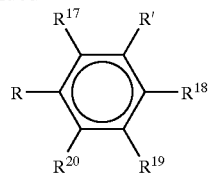

In general formulae (2)' to (4)', $R^{17}$ to $R^{24}$ are the same as in general formulae (2) to (4), and R and R' are the same as in general formula (1)'.

Examples of the monomers (A) represented by general formula (1)' include 4,4'-dichlorobenzophenone, 2,4'-dichlorobenzophenone, 3,3'-dichlorobenzophenone,
4,4'-dibromobenzophenone, 2,4'-dibromobenzophenone, 3,3'-dibromobenzophenone,
4,4'-diiodobenzophenone, 2,4'-diiodobenzophenone, 3,3'-diiodobenzophenone,
bis(4-trifluoromethylsulfonyloxyphenyl) ketone,
bis(3-trifluoromethylsulfonyloxy-phenyl) ketone,
4,4'-bis(4-chlorobenzoyl)diphenyl ether,
4,4'-bis(3-chlorobenzoyl)diphenyl ether, 4,4'-bis(4-bromobenzoyl)diphenyl ether,
4,4'-bis(3-bromobenzoyl)diphenyl ether, 4,4'-bis(4-iodobenzoyl)diphenyl ether,
4,4'-bis(3-iodobenzoyl)diphenyl ether,
4,4'-bis(4-trifluoromethylsulfonyloxyphenyl)diphenyl ether,
4,4'-bis(3-trifluoromethylsulfonyloxyphenyl)diphenyl ether,
4,4'-bis(4-methylsulfonyloxyphenyl)diphenyl ether,
4,4'-bis(3-methylsulfonyloxyphenyl)diphenyl ether,
4'-bis(4-chlorobenzoylamino)diphenyl ether,
3,4'-bis(4-chlorobenzoylamino)diphenyl ether,
4,4'-bis(3-chlorobenzoylamino)diphenyl ether, 3,4'-bis(3-chlorobenzoyl)diphenyl ether,
4,4'-bis(4-bromobenzoylamino)diphenyl ether,
3,4'-bis(4-bromobenzoylamino)diphenyl ether,
4,4'-bis(3-bromobenzoylamino)diphenyl ether,
3,4'-bis(3-bromobenzoylamino)diphenyl ether,
4,4'-bis(4-iodobenzoylamino)diphenyl ether,
3,4'-bis(4-iodobenzoylamino)diphenyl ether,
4,4'-bis(3-iodobenzoylamino)diphenyl ether,
3,4'-bis(3-iodobenzoylamino)diphenyl ether,
4,4'-bis(4-trifluoromethylsulfonyloxyphenyl)diphenyl ether,
3,4'-bis(4-trifluoromethylsulfonyloxyphenyl)diphenyl ether,
4,4'-bis(3-trifluoromethylsulfonyloxyphenyl)diphenyl ether,
3,4'-bis(3-trifluoromethylsulfonyloxyphenyl)diphenyl ether,
4,4'-bis(4-methylsulfonyloxyphenyl)diphenyl ether,
3,4'-bis(4-methylsulfonyloxyphenyl)diphenyl ether,
4,4'-bis(3-methylsulfonyloxyphenyl)diphenyl ether,
3,4'-bis(3-methylsulfonyloxyphenyl)diphenyl ether,
4,4'-bis(4-chlorophenylsulfonyl)diphenyl ether,
3,4'-bis(4-chlorophenylsulfonyl)diphenyl ether,
4,4'-bis(3-chlorophenylsulfonyl)diphenyl ether,
3,4'-bis(3-chlorophenylsulfonyl)diphenyl ether,
4,4'-bis(4-bromophenylsulfonyl)diphenyl ether,
3,4'-bis(4-bromophenylsulfonyl)diphenyl ether,
4,4'-bis(3-bromophenylsulfonyl)diphenyl ether,
3,4'-bis(3-bromophenylsulfonyl)diphenyl ether,
4,4'-bis(4-iodophenylsulfonyl)diphenyl ether,
4,4'-bis(4-iodophenylsulfonyl)diphenyl ether,
4,4'-bis(3-iodophenylsulfonyl)diphenyl ether,
3,4'-bis(3-iodophenylsulfonyl)diphenyl ether,
4,4'-bis(4-trifluoromethylsulfonyloxyphenylsulfonyl) diphenyl ether, 4,4'-bis(4-trifluoromethylsulfonyloxyphenylsulfonyl) diphenyl ether,
4,4'-bis(3-trifluoromethylsulfonyloxyphenylsulfonyl)- diphenyl ether,
3,4'-bis(3-trifluoromethylsulfonyloxyphenylsulfonyl)- diphenyl ether,
4,4'-bis(4-methylsulfonyloxyphenylsulfonyl)-diphenyl ether,
4,4'-bis(4-methylsulfonyloxyphenylsulfonyl)-diphenyl ether,
4,4'-bis(3-methylsulfonyloxyphenylsulfonyl)-diphenyl ether,
3,4'-bis(3-methylsulfonyloxyphenylsulfonyl)-diphenyl ether,
4,4'-bis(4-chlorophenyl)diphenyl ether dicarboxylate,
3,4'-bis(4-chlorophenyl)diphenyl ether dicarboxylate,
4,4'-bis(3-chlorophenyl)diphenyl ether dicarboxylate,
3,4'-bis(3-chlorophenyl)diphenyl ether dicarboxylate,
4,4'-bis(4-bromophenyl)diphenyl ether dicarboxylate,
3,4'-bis(4-bromophenyl)diphenyl ether dicarboxylate,
4,4'-bis(3-bromophenyl)diphenyl ether dicarboxylate,
3,4'-bis(3-bromophenyl)diphenyl ether dicarboxylate,
4,4'-bis(4-iodophenyl)diphenyl ether dicarboxylate,
3,4'-bis(4-iodophenyl)diphenyl ether dicarboxylate,
4,4'-bis(3-iodophenyl)diphenyl ether dicarboxylate,
3,4'-bis(3-iodophenyl)diphenyl ether dicarboxylate,
4,4'-bis(4-trifluoromethylsulfonyloxyphenyl)diphenyl ether dicarboxylate,
3,4'-bis(4-trifluoromethylsulfonyloxyphenyl)diphenyl ether dicarboxylate,
4,4'-bis(3-trifluoromethylsulfonyloxyphenyl)diphenyl ether dicarboxylate,
3,4'-bis(3-trifluoromethylsulfonyloxyphenyl)diphenyl ether dicarboxylate,
4,4'-bis(4-methylsulfonyloxyphenyl)diphenyl ether dicarboxylate,
3,4'-bis(4-methylsulfonyloxyphenyl)diphenyl ether dicarboxylate,
4,4'-bis(3-methylsulfonyloxyphenyl)diphenyl ether dicarboxylate,
3,4'-bis(3-methylsulfonyloxyphenyl)diphenyl ether dicarboxylate,
4,4'-bis[(4-chlorophenyl)-1,1,1,3,3,3-hexafluoropropyl] diphenyl ether,
3,4'-bis[(4-chlorophenyl)-1,1,1,3,3,3-hexafluoropropyl] diphenyl ether,
4,4'-bis[(3-chlorophenyl)-1,1,1,3,3,3-hexafluoropropyl] diphenyl ether,
3,4'-bis[(3-chlorophenyl)-1,1,1,3,3,3-hexafluoropropyl] diphenyl ether,
4,4'-bis[(4-bromophenyl)-1,1,1,3,3,3-hexafluoropropyl] diphenyl ether,
3,4'-bis[(4-bromophenyl)-1,1,1,3,3,3-hexafluoropropyl] diphenyl ether,
4,4'-bis[(3-bromophenyl)-1,1,1,3,3,3-hexafluoropropyl] diphenyl ether,
3,4'-bis[(3-bromophenyl)-1,1,1,3,3,3-hexafluoropropyl] diphenyl ether,
4,4'-bis[(4-iodophenyl)-1,1,1,3,3,3-hexafluoropropyl] diphenyl ether,
3,4'-bis[(4-iodophenyl)-1,1,1,3,3,3-hexafluoropropyl] diphenyl ether,
4,4'-bis[(3-iodophenyl)-1,1,1,3,3,3-hexafluoropropyl] diphenyl ether,
3,4'-bis[(3-iodophenyl)-1,1,1,3,3,3-hexafluoropropyl] diphenyl ether,
4,4'-bis[(4-trifluoromethylsulfonyloxyphenyl)-1,1,1,3,3,3-hexafluoropropyl]diphenyl ether,
3,4'-bis[(4-trifluoromethylsulfonyloxyphenyl)-1,1,1,3,3,3-hexafluoropropyl]diphenyl ether,
4,4'-bis[(3-trifluoromethylsulfonyloxyphenyl)-1,1,1,3,3,3-hexafluoropropyl]diphenyl ether,
3,4'-bis [(3-trifluoromethylsulfonyloxyphenyl)-1,1,1,3,3,3-hexafluoropropyl]diphenyl ether,
4,4'-bis[(4-methylsulfonyloxyphenyl)-1,1,1,3,3,3-hexafluoropropyl]diphenyl ether,
3,4'-bis[(4-methylsulfonyloxyphenyl)-1,1,1,3,3,3-hexafluoropropyl]diphenyl ether,
4,4'-bis[(3-methylsulfonyloxyphenyl)-1,1,1,3,3,3-hexafluoropropyl]diphenyl ether,
3,4'-bis[(3-methylsulfonyloxyphenyl)-1,1,1,3,3,3-hexafluoropropyl]diphenyl ether,
4,4'-bis[(4-chlorophenyl)tetrafluoroethyl]diphenyl ether,
4,4'-bis[(3-chlorophenyl)tetrafluoroethyl]diphenyl ether,
4,4'-bis[(4-chlorophenyl)hexafluoropropyl]diphenyl ether,
4,4'-bis[(3-chlorophenyl)hexafluoropropyl]diphenyl ether,
4,4'-bis[(4-chlorophenyl)octafluorobutyl]diphenyl ether,
4,4'-bis[(3-chlorophenyl)octafluorobutyl]diphenyl ether,
4,4'-bis[(4-chlorophenyl)decafluoropentyl]diphenyl ether,
4,4'-bis[(3-chlorophenyl)decafluoropentyl]diphenyl ether,
4,4'-bis[(4-bromophenyl)tetrafluoroethyl]diphenyl ether,
4,4'-bis[(3-bromophenyl)tetrafluoroethyl]diphenyl ether,
4,4'-bis[(4-bromophenyl)hexafluoropropyl]diphenyl ether,
4,4'-bis[(3-bromophenyl)hexafluoropropyl]diphenyl ether,
4,4'-bis[(4-bromophenyl)octafluorobutyl]diphenyl ether,
4,4'-bis[(3-bromophenyl)octafluorobutyl]diphenyl ether,
4,4'-bis[(4-bromophenyl)decafluoropentyl]diphenyl ether,
4,4'-bis[(3-bromophenyl)decafluoropentyl]diphenyl ether,
4,4'-bis[(4-iodophenyl)tetrafluoroethyl]diphenyl ether,
4,4'-bis[(3-iodophenyl)tetrafluoroethyl]diphenyl ether,
4,4'-bis[(4-iodophenyl)hexafluoropropyl]diphenyl ether,
4,4'-bis[(3-iodophenyl)hexafluoropropyl]diphenyl ether,
4,4'-bis[(4-iodophenyl)octafluorobutyl]diphenyl ether,
4,4'-bis[(3-iodophenyl)octafluorobutyl]diphenyl ether,
4,4'-bis[(4-iodophenyl)decafluoropentyl]diphenyl ether,
4,4'-bis[(3-iodophenyl)decafluoropentyl]diphenyl ether,
4,4'-bis[(4-trifluoromethylsulfonyloxyphenyl) tetrafluoroethyl]iphenyl ether,
4,4'-bis[(3-trifluoromethylsulfonyloxy-phenyl) tetrafluoroethyl]diphenyl ether,
4,4'-bis[(4-trifluoromethylsulfonyloxyphenyl) hexafluoropropyl]diphenyl ether,
4,4'-bis[(3-trifluoromethylsulfonyloxyphenyl) hexafluoropropyl]diphenyl ether,
4,4'-bis[(4-trifluoromethylsulfonyloxyphenyl) octafluorobutyl]diphenyl ether,
4,4'-bis[(3-trifluoromethylsulfonyloxyphenyl) octafluorobutyl]diphenyl ether,
4,4'-bis[(4-trifluoromethylsulfonyloxyphenyl) decafluoropentyl]diphenyl ether,
4,4'-bis[(3-trifluoromethylsulfonyloxyphenyl) decafluoropentyl]diphenyl ether,
4,4'-bis[(4-methylsulfonyloxyphenyl)tetrafluoroethyl] diphenyl ether,
4,4'-bis[(3-methylsulfonyloxyphenyl)tetrafluoroethyl] diphenyl ether,
4,4'-bis[(4-methylsulfonyloxyphenyl)-hexafluoropropyl] diphenyl ether,
4,4'-bis[(3-methylsulfonyloxyphenyl)hexafluoropropyl] diphenyl ether,
4,4'-bis[(4-methylsulfonyloxyphenyl)octafluorobutyl] diphenyl ether,
4,4'-bis[(3-methylsulfonyloxyphenyl)octafluorobutyl] diphenyl ether,
4,4'-bis[(4-methylsulfonyloxyphenyl)-decafluoropentyl] diphenyl ether, and 4,4'-bis[(3-methylsulfonyloxyphenyl)decafluoropentyl] diphenyl ether.

On the other hand, examples of the monomers (B) represented by general formula (2)' include p-dichlorobenzene, p-dibromobenzene, p-diiodobenzene, p-dimethylsulfonyloxybenzene, 2,5-dichlorotoluene, 2,5-dibromotoluene, 2,5-diiodotoluene, 2,5-dimethylsulfonyloxybenzene, 2,5-dichloro-p-xylene, 2,5-dibromo-p-xylene, 2,5-diiodo-p-xylene, 2,5-dichlorobenzotrifluoride, 2,5-dibromobenzotrifluoride, 2,5-diiodobenzotrifluoride, 1,4-dichloro-2,3,5,6-tetrafluorobenzene, 1,4-dibromo-2,3,5,6-tetrafluorobenzene, 1,4-diiodo-2,3,5,6-tetrafluorobenzene, 4'-phenoxy-2,5-dichlorobenzophenone, and 4'-phenoxyphenyl 2,5-dichlorobenzoate. Preferred of these are p-dichlorobenzene, p-dimethylsulfonyloxybenzene, 2,5-dichlorotoluene, 2,5-dichlorobenzotrifluoride, 4'-phenoxy-2,5-dichlorobenzophenone, and 4'-phenoxyphenyl 2,5-dichlorobenzoate.

Examples of the monomers (B) represented by general formula (3)' include 4,4'-dimethylsulfonyloxybiphenyl, 4,4'-dimethylsulfonyloxy-3,3'-dipropenylbiphenyl, 4,4'-dibromobiphenyl, 4,4'-diiodobiphenyl, 4,4'-dimethylsulfonyloxy-3,3'-dimethylbiphenyl, 4,4'-dimethylsulfonyloxy-3,3'-difluorobiphenyl, 4,4'-dimethylsulfonyloxy-3,3',5,5'-tetrafluorobiphenyl, 4,4'-dibromooctafluorobiphenyl, and 4,4'-(4-methylsulfonyloxyphenyloctafluorobiphenyl. Preferred of these are 4,4'-dimethylsulfonyloxybiphenyl, 4,4'-dibromobiphenyl, 4,4'-diiodobiphenyl, and 4,4'-dimethylsulfonyloxy-3,3'-dipropenylbiphenyl.

Examples of the monomers (B) represented by general formula (4)' include m-dichlorobenzene, m-dibromobenzene, m-diiodobenzene, m-dimethylsulfonyloxybenzene, 2,4-dichlorotoluene, 2,4-dibromotoluene, 2,4-diiodotoluene, 3,5-dichlorotoluene, 3,5-dibromotoluene, 3,5-diiodotoluene, 2,6-dichlorotoluene, 2,6-dibromotoluene, 2,6-diiodotoluene, 3,5-dimethylsulfonyloxytoluene, 2,6-dimethylsulfonyloxytoluene, 2,4-dichlorobenzotrifluoride, 2,4-dibromobenzotrifluoride, 2,4-diiodobenzotrifluoride, 3,5-dichlorobenzotrifluoride, 3,5-dibromobenzotrifluoride, 3,5-diiodobenzotrifluoride, 1,3-dibromo-2,4,5,6-tetrafluorobenzene, 2,4-dichloro-4'-phenoxybenzophenone, and 2,4-dichloro-4'-phenoxyphenyl benzoate. Preferred of these are m-dichlorobenzene, 2,4-dichlorotoluene, 3,5-dimethylsulfonyloxytoluene, 2,4-dichlorobenzotrifluoride, 2,4-dichloro-4'-phenoxybenzophenone, and 2,4-dichloro-4'-phenoxyphenyl benzoate.

Preferred of the aforementioned monomers (B) represented by general formulae (2)' to (4)' from the standpoints of solubility and production of a polymer having a high molecular weight are 2,5-dichloro-4'-phenoxybenzophenone, 2,4-dichloro-4'-phenoxybenzophenone, 2,5-dichloro-4'-phenoxyphenyl benzoate, and 2,4-dichloro-4'-phenoxyphenyl benzoate.

The proportion of monomers (A), which is at least one compound represented by general formula (1)', to monomers (B), which is at least one of aromatic compounds represented by general formulae (2)' to (4)', to be copolymerized is the same as the proportion of units (A) to units (B) described above. Namely, monomers (A) is used in an amount of 60 mol % or less, preferably 40 to 0.01 mol %, while monomers (B) is used in an amount of 40 mol % or more, preferably 60 to 99.99 mol %.

In particular, in the case where monomers (B) represented by general formula (2)' is used, the proportion thereof is preferably 10 mol % or larger, more preferably 20 mol % or larger, based on all monomers. When the proportion of monomers (B) represented by general formula (2)' is within that range, polymers having high molecular weights and satisfactory solubility is obtained.

In the case where monomers (B) represented by general formula (3)' is used, the proportion thereof is preferably 50 mol % or smaller, more preferably 30 mol % or smaller, based on all monomers. When the proportion of this monomer is within that range, polymers having high molecular weights and satisfactory solubility is obtained.

Furthermore, in the case where monomers (B) represented by general formula (4)' is used, the proportion thereof is preferably 50 mol % or smaller, more preferably 30 mol % or smaller, based on all monomers.

The catalyst to be used in producing the polyarylene copolymers of the invention is a catalyst system containing transition metal compounds. The catalyst systems comprise as essential ingredients (1) either a combination of a transition metal salt and one or more ligands or a transition metal (salt) having one or more ligands coordinated thereto and (2) a reducing agent. A salt may be added to the catalyst system in order to heighten the rate of polymerization.

Examples of the transition metal salt include nickel compounds such as nickel chloride, nickel bromide, nickel iodide, and nickel acetylacetonate, palladium compounds such as palladium chloride, palladium bromide, and palladium iodide, iron compounds such as iron chloride, iron bromide, and iron iodide, and cobalt compounds such as cobalt chloride, cobalt bromide, and cobalt iodide. Especially preferred of these are nickel chloride and nickel bromide.

Examples of the ligands include triphenylphosphine, 2,2'-bipyridine, 1,5-cyclooctadiene, and 1,3-bis(diphenylphosphino)propane. Preferred of these are triphenylphosphine and 2,2'-bipyridine. These ligands may be used alone or in combination of two or more thereof.

Examples of the transition metals (salts) having one or more ligands coordinated thereto include nickel chloride bis(triphenylphosphine), nickel bromide bis(triphenylphosphine), nickel iodide bis(triphenylphosphine), nickel nitrate bis(triphenylphosphine), nickel chloride 2,2'-bipyridine, nickel bromide 2,2'-bipyridine, nickel iodide 2,2'-bipyridine, nickel nitrate 2,2'-bipyridine, bis(1,5-cyclooctadiene)nickel, tetrakis(triphenylphosphine)nickel, tetrakis(triphenylphosphite)nickel, and tetrakis (triphenylphosphine)palladium. Preferred of these are nickel chloride bis(triphenylphosphine) and nickel chloride 2,2'-bipyridine.

Examples of the reducing agents which can be used in the catalyst systems according to the invention include iron, zinc, manganese, aluminum, magnesium, sodium, and calcium. Preferred of these are zinc, magnesium, and manganese. These reducing agents can be used after having been further activated by contact with an acid, e.g., an organic acid.

Examples of the salts which can be optionally used in the catalyst systems according to the invention include sodium compounds such as sodium fluoride, sodium chloride, sodium bromide, sodium, iodide, and sodium sulfate, potassium compounds such as potassium fluoride, potassium chloride, potassium bromide, potassium iodide, and potassium sulfate, and ammonium compounds such as tetraethylammonium fluoride, tetraethylammonium chloride, tetraethylammonium bromide, tetraethylammonium iodide, and tetraethylammonium sulfate. Preferred of these are sodium bromide, sodium iodide, potassium bromide, tetraethylammonium bromide, and tetraethylammonium iodide.

In the catalyst systems, the proportions of the ingredients to be used therein are as follows. The proportion of either the transition metal salts or the transition metals (salts) having one or more ligands coordinated thereto is generally from 0.0001 to 10 mol, preferably from 0.01 to 0.5 mol, per mol of all the monomers represented by general formulae (1)' to (4)'. When the proportion thereof is smaller than 0.0001 mol, the polymerization reaction does not proceed sufficiently. On the other hand, proportions thereof exceeding 10 mol pose such a problem that the polymerization yields a polymer having low molecular weight.

In the case where the catalyst system contains a transition metal salts and one or more ligands, the proportion of the ligands is generally from 0.1 to 100 mol, preferably from 1 to 10 mol, per mol of the transition metal salts. When the proportion thereof is smaller than 0.1 mol, the result is insufficient catalytic activity. On the other hand, proportions thereof exceeding 100 mol pose such a problem that the polymerization yields polymer with a low molecular weight.

The proportion of the reducing agents to be used in the catalyst systems are generally from 0.1 to 100 mol, preferably from 1 to 10 mol, per mol of all the monomers represented by general formulae (1)' to (4)'. When the proportion thereof is smaller than 0.1 mol, the polymerization does not proceed sufficiently. On the other hand, proportions thereof exceeding 100 mol pose a problem that the polymer obtained is difficult to purify.

In the case where the salts as an optional ingredient are used in the catalyst system, the proportion thereof is generally from 0.001 to 100 mol, preferably from 0.01 to 1 mol, per mol of all the monomers represented by general formulae (1)' to (4)'. When the proportion thereof is smaller than 0.001 mol, the effect of heightening the rate of polymerization is insufficient. On the other hand, proportions thereof exceeding 100 mol pose such a problem that the polymer obtained is difficult to purify.

In the invention, the monomers (A) and the monomers (B) can be reacted in the presence of a molecular weight modifier, thereby controlling a molecular weight of the polymer obtained.

The molecular weight modifier is a monomer having only one reaction site (such as monohalogenated aromatic compounds or monosulfonate compounds) in order to stop increase in molecular weight of the polyarylene obtained. The molecular weight modifier is represented by general formula such as R-φ, R-φ-T or R-φ-T-φ, wherein R is a group represented by halogen atom or —OSO$_2$Z (wherein Z represents alkyl group, halogenated alkyl group or aryl group), φ is benzene nucleus, and T is monovalent or divalent electron-withdrawing groups, where examples of the monovalent groups include —CN, —NO$_2$ and —CONR"$_2$ (wherein R" represents alkyl group or aryl group), and examples of the divalent groups include —CO—, —CONH—, —SO$_2$, —SO—, —C(CF$_3$)—, —, —C(CF$_3$)(C$_6$H$_5$)— and —COO—.

Preferable examples of the molecular weight modifier include monohalogented aromatic compounds such as 4-chlrobenzophenoe, 4-chlorobenzanilide, chlrorbenzene, bromobenzene, 4-bromobenzophenone, phenyl 4-chlorobenzoate, phenyl 4-bromobenzoate, 4-chlorophenyl benzoate, 4-bromphenyl benzoate, 2,2-chlorophenyl-phenylhexafluoropropane and 1,1,1-diphenylchlorophenyltrifluoromethane, and monosulfonate compounds such as chlorophenylphenylsulfone, 4-sulfonyloxybenzophenone and 4-sulfonylxydiphenylsulfone. In the invention, halogen atom that the monohalogenated aromatic compounds have is preferably chlorine atom or bromine atom.

Amount of the molecular weight modifier used is 0.1 to 100 mmol, preferably 0.5 to 30.0 mmol, pre mole of the sum of the monomers (A) and monomers (B). If the amount is less than 0.1 mmol, the effect to increase molecular weight is not exhibited, and if the amount exceeds 100 mmol, molecular weight remarkably decreases.

Examples of polymerization solvents which can be used in the invention include tetrahydrofuran, cyclohexanone, dimethyl sulfoxide, N,N-dimethylformamide, N,N-dimethylacetamide, N-methyl-2-pyrrolidone and γ-butyrolactam. Preferred of these are tetrahydrofuran, N,N-dimethylformamide, N,N-dimethylacetamide, and N-methyl-2-pyrrolidone. It is preferred to sufficiently dry these polymerization solvents before use.

The concentration of all the monomers represented by general formulae (1)' to (4)' in the polymerization solvent is generally from 1 to 90% by weight, preferably from 5 to 40% by weight.

The polymerization for preparing the polymer of the invention is conducted at a temperature of generally from 0 to 200° C., preferably from 50 to 80° C., for a period of usually from 0.5 to 100 hours, preferably from 1 to 40 hours.

In the case where monomers (A) represented by general formula (1)' and monomers (B) represented by general formula (2)' are used for obtaining a polymer consisting of repeating structural units represented by general formulae (1) and (2) (provided that the units have no sulfonic acid groups), an example of the reaction schemes is as follows.

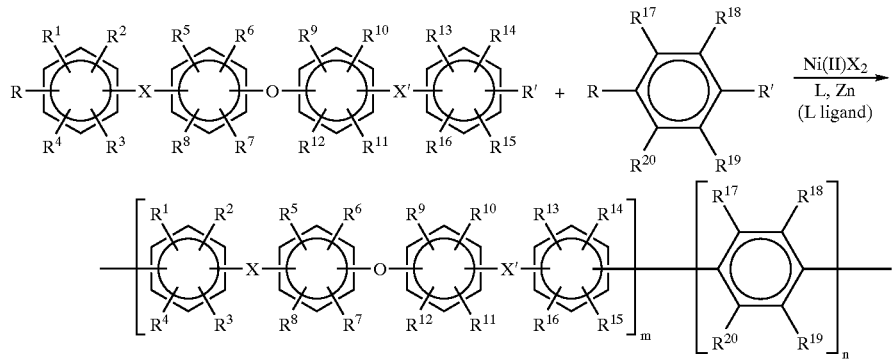

The structure of the polyarylene copolymers of the invention can be ascertained, for example, from infrared absorption spectra based on the C—O—C stretching appearing at 1,230 to 1,250 cm$^{-1}$, the C=O stretching appearing at 1,640 to 1,660 cm$^{-1}$, etc., or from a nuclear magnetic resonance ($^1$H-NMR) based on the peak assigned to aromatic protons appearing at 6.8 to 8.0 ppm.

The polyarylene copolymers having sulfonic acid groups for use as the conductive membrane of the invention can be obtained by incorporating sulfonic acid groups into the above-described polyarylene copolymers having no sulfonic acid groups by an ordinary method using a sulfonating agent.

For example, sulfonic acid groups can be incorporated by sulfonating the polyarylene copolymers having no sulfonic acid groups with known sulfonating agents such as sulfuric acid anhydride, fuming sulfuric acid, chlorosulfonic acid, sulfuric acid, or sodium hydrogen sulfite under known conditions [see *Polymer Preprints*, Japan, Vol. 42, No. 3, p. 730 (1993); *Polymer Preprints*, Japan, Vol. 42, No. 3, p. 736 (1994); and *Polymer Preprints*, Japan, Vol. 42, No. 7, pp. 2490-2492 (1993)].

Specifically, the reaction conditions for this sulfonation are as follows. The polyarylene copolymer having no sulfonic acid groups is reacted with the sulfonating agent in the presence or absence of a solvent. Examples of the solvent include hydrocarbon solvents such as n-hexane, ether solvents such as tetrahydrofuran and dioxane, aprotic polar solvents such as N,N-dimethylacetamide, N,N-dimethylformamide, N-methyl-2-pyrrolidone, and dimethyl sulfoxide, and halogenated hydrocarbons such as tetrachloroethane, dichloroethane, chloroform, and methylene chloride. Although the reaction temperature is not particularly limited, it is generally from −50 to 200° C., preferably from −10 to 100° C. The reaction period is generally from 0.5 to 1,000 hours, preferably from 1 to 200 hours.

Thus, copolymers comprising units (A) and units (B) and having sulfonic acid groups are obtained. The amount of the sulfonic acid groups contained in the polymer is generally from 1 to 5 meq, preferably from 1.5 to 4 meq, per g of the polymer. In other words, in the sulfonic acid-containing polymer of the invention, the number of sulfonic acid groups contained therein is generally from 0.05 to 2, preferably from 0.3 to 1.5, per unit (B) as a component of the polymer. When the number of sulfonic acid groups is smaller than 0.05 per unit (B) as a component of the polymer, proton conductivity is insufficient. On the other hand, when the number thereof exceeds 2 per unit (B), hydrophilicity is enhanced, so that the polymer is soluble in water or, even when remaining water-insoluble, has reduced durability.

Desirable examples of the sulfonic acid-containing copolymers are:

copolymers which comprise preferably from 40 to 3 mol %, more preferably from 30 to 5 mol %, structural units derived from 4,4'-bis(4-chloro)diphenyl ether as units (A) and preferably from 60 to 97 mol %, more preferably from 70 to 95 mol %, structural units derived from 2,5-dichloro-4'-phenoxybenzophenone as units (B) and which has sulfonic acid groups in an amount of preferably from 1.5 to 3.5 meq, more preferably from 2.0 to 3.3 meq, per g of the polymer; and copolymers which comprise preferably from 35 to 7 mol %, more preferably from 30 to 8 mol %, structural units derived from 4,4'-dichlorobenzophenone as units (A) and preferably from 65 to 93 mol %, more preferably from 70 to 92 mol %, structural units derived from 2,5-dichloro-4'-phenoxybenzophenone as units (B) and which has sulfonic acid groups in an amount of preferably from 2.0 to 3.5 meq, more preferably from 2.0 to 3.3 meq, per g of the polymer.

The amount of sulfonic acid groups to be incorporated can be easily regulated by changing the amount (proportion) of monomer (A) to be used as comonomers for forming aromatic compound units having a main chain containing one or more electron-withdrawing groups therein.

The molecular weight of the unsulfonated polyarylene copolymer, from which the sulfonic acid-containing copolymers of the invention is obtained by the method described above, is generally from 1,000 to 1,000,000, preferably from 1,500 to 200,000, in terms of weight-average molecular weight calibrated for that of standard polystyrenes. When the molecular weight thereof is lower than 1,000, the polymer not only has insufficient membrane-forming properties to give a membrane having cracks, but has insufficient strength properties. On the other hand, when the molecular weight thereof exceeds 1,000,000, the polymer has problems of insufficient solubility, too high a solution viscosity, poor processability, etc.

The structure of the copolymers having sulfonic acid groups of the invention can be ascertained from an infrared spectra based on the S=O absorption appearing at 1,030 to 1,045 cm$^{-1}$ and at 1,160 to 1,190 cm$^{-1}$, the C—O—C stretching appearing at 1,130 to 1,250 cm$^{-1}$, the C=O stretching appearing at 1,640 to 1,660 cm$^{-1}$, etc. The composition of sulfonic acid in copolymers can be determined by titration based on neutralization of the sulfonic acid or by elemental analysis. The structure of the copolymer can be ascertained also from a nuclear magnetic resonance ($^1$H-NMR) spectrum based on the peak assigned to aromatic protons appearing at 6.8 to 8.0 ppm.

The proton-conductive membrane of the invention comprises the copolymers containing sulfonic acid groups described above. However, the copolymers containing sulfonic acid groups may be used in combination with an inorganic acid such as sulfuric acid or phosphoric acid, an organic acid such as a carboxylic acid, an appropriate amount of water, etc.

Examples of methods for producing the proton-conductive membrane of the invention include a casting method and a melt forming method. In the casting method, the copolymers containing sulfonic acid groups of the invention is dissolved in solvents and the solution is formed into membrane by casting.

Examples of the solvents used in the casting method include aprotic polar solvents such as N,N-dimethylacetamide, N,N-dimethylformamide, N-methyl-2-pyrrolidone, and dimethyl sulfoxide and alcohol solvents such as methanol.

The proton-conductive, membrane of the invention can be utilized as a proton-conductive membrane in applications such as, e.g., electrolytes for primary batteries, electrolytes for secondary batteries, solid polymer electrolytes for fuel cells, display elements, various sensors, signal-transmitting media, solid capacitors, and ion-exchange membranes.

The invention will be explained below in more detail by reference to Examples, but the invention should not be construed as being limited to the following Examples.

In the Examples, various properties were determined by the following methods.

Weight-Average Molecular Weight

The number-average molecular weight or weight-average molecular weight of a precursor polymer to be sulfonated was determined, in terms of molecular weight calibrated for standard polystyrene, by gel permeation chromatography (GPC) using tetrahydrofuran (THF) as a solvent.

Equivalent Weight for Sulfonic Acid

A polymer obtained was sufficiently washed with water until the washing water became near neutral to thereby remove the remaining free acid. The polymer washed was dried, and a given amount thereof was weighed and dissolved in a THF/water mixed solvent. This solution was titrated with a standard NaOH solution using phenolphthalein as an indicator. The equivalent weight for sulfonic acid of the polymer was determined from the neutralization point.

Measurement of Proton Conductivity

A sample of membrane having a diameter of 13 mm which had been placed in an atmosphere having a relative humidity of 100% was sandwiched between platinum electrodes. This sandwich was placed in a closed cell, which was examined with an impedance analyzer (HYP4192A) for the absolute value of cell impedance and for phase angle under the conditions of-a frequency of from 5 to 13 MHz, applied voltage of 12 mV, and temperature of 20° C., 50° C., or 100° C. The data obtained were used to determine the complex impedance at an oscillation level of 12 mV with a computer. The proton conductivity of the sample was calculated therefrom.

Tensile Strength

The tensile strength of a membrane obtained was measured by conventional tensile test at room temperature.

Behavior in Hot Water

The behavior of a membrane in hot water was observed by immersing the membrane in 80° C. water for 24 hours and then examining the membrane for any changes in shape or state.

○: The membrane had a swell lower than 20% and retained the shape.

Δ: The membrane had a swell of 20% or higher and retained the shape.

×: The shape was not retained.

REFERENCE EXAMPLE 1

[Synthesis of 3,4'-bis(4-chlorobenzoylamino)diphenyl Ether]

A stirrer, three-way cock, and dropping funnel were attached to a three-necked flask containing 28.0 g (140 mmol) of 3,4'-diaminodiphenyl ether. The atmosphere in the flask was replaced with dry nitrogen. Thereto were added 200 ml of N-methylpyrrolidone and 28.3 g (280 mmol) of triethylamine. The resulting mixture was stirred. This flask was placed on an ice bath to cool the reaction mixture to 0° C. Thereafter, 53.9 g (308 mmol) of 4-chlorobenzoyl chloride was added thereto through the dropping funnel over 30 minutes. This mixture was further stirred on the ice bath for 30 minutes, subsequently allowed to gradually warm up to room temperature, and then continued to react for 12 hours. The resulting reaction mixture was poured into 1.5 L of 4% aqueous sodium hydrogen carbonate solution. The precipitate yielded was taken out by filtration, washed with water, and then dried. The powder obtained was dissolved in 300 ml of N-methylpyrrolidone and reprecipitated from 1 liter of methanol. The product was recovered by filtration and dried to obtain 66 g (yield, 99%) of the target compound. It showed a melting point of from 258 to 259° C.

REFERENCE EXAMPLE 2

[Synthesis of 4,4'-bis(4-chlorobenzoyl)diphenyl Ether]

A solution prepared by dissolving 42.6 g (250 mmol) of diphenyl ether and 87.5 g (500 mmol) of 4-chlorobenzoyl chloride in 75 ml of methylene chloride was placed in a three-necked flask equipped with a dropping funnel, stirrer, and three-way cock. In a dry nitrogen atmosphere, a suspension obtained by dispersing 83.3 g (625 mmol) of anhydrous aluminum chloride in 75 ml of methylene chloride was added dropwise to the solution with stirring and under cooling at 10° C. or lower over 2 hours to react the reactants. The red-brown solution obtained after the dropwise addition was continuously reacted at room temperature for 10 hours and then poured into an ice bath containing hydrochloric acid (a mixture of 2 kg of ice and 200 ml of aqueous hydrochloric acid solution) to cause precipitation. The precipitate was recovered by filtration and then dried. The powder obtained was pulverized and washed with 1 N aqueous hydrochloric acid solution, 5% aqueous sodium hydrogen carbonate solution, and distilled water. The crude crystalline product was dissolved in toluene and dehydrated by azeotropic distillation to obtain a concentrated solution. The concentrated solution was filtered through a hot Buchner funnel and the filtrate was cooled. Thus, 49 g of the target compound was obtained as crystals; the yield was 44%.

EXAMPLE 1

Into a three-necked flask equipped with a ball condenser and a three-way cock were introduced 193.5 g (540 mmol) of 2,5-dichloro-4'-phenoxybenzophenone, 28.64 g (60 mmol) of 3,4'-bis(4-chlorobenzoylamino)diphenyl ether, 11.7 g (78 mmol) of sodium iodide, 11.8 g (18 mmol) of bis(triphenylphosphine)nickel dichloride, 63.0 g (240 mmol) of triphenylphosphine, and 94.1 g (1.44 mol) of zinc. This flask was placed on a 70° C. oil bath and the atmosphere in the flask was replaced with nitrogen. Thereafter, 1,000 ml of N-methyl-2-pyrrolidone was added to the mixture under a nitrogen atmosphere to initiate a reaction. The reaction mixture was reacted for 20 hours and then diluted with 500 ml of N-methyl-2-pyrrolidone. The resulting reaction mixture which had undergone polymerization was poured into a 1:10 mixture of hydrochloric acid and methanol to precipitate polymer. The precipitates were washed, recovered by filtration, and then dried in vacuo. Thus, 173.3 g of a white powder was obtained. This polymer had a weight-average molecular weight of 123,000. The polymer obtained was formed into membrane using N-methyl-2-pyrrolidone as casting solvent. This membrane was immersed in methanol, but no swelling was observed.

1,500 ml of concentrated sulfuric acid was added to 150 g of the polyarylene copolymer obtained above. This mixture was stirred at room temperature for 24 hours to sulfonation. After the reaction, the reaction mixture was poured into a large amount of pure water to precipitate the sulfonated polymer. The resulting polymer was washed with water until the washing water became nearly neutral. Thereafter, the sulfonated polymer was recovered by filtration and dried in vacuo at 90° C. 185.2 g of the sulfonated polymer was obtained. An IR spectrum thereof is shown in FIG. 1.

EXAMPLE 2

Reaction was conducted in the same manner as in Example 1, except that the amounts of the feed monomers, i.e., 2,5-dichloro-4'-phenoxybenzophenone and 3,4'-bis(4-chlorobenzoylamino)diphenyl ether, were changed to 172.00 g (480 mmol) and 57.27 g (120 mmol), respectively. As a result, a polymer was obtained in an amount of 177.3 g. It had a weight-average molecular weight of 133,500.

Figure 2:
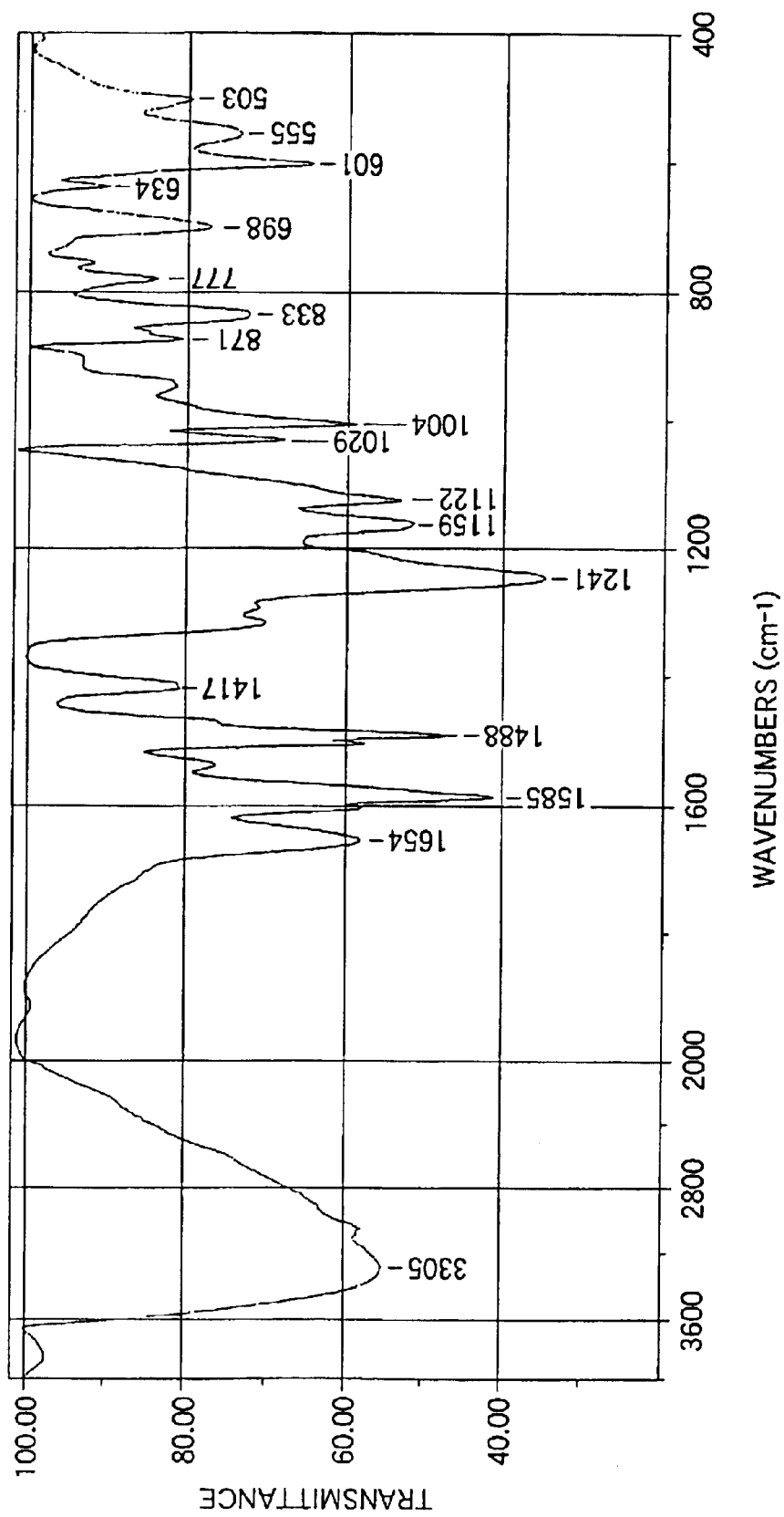
FIG. 2 is an IR chart of the sulfonated polymer obtained in Example 2.

A 150 g portion of the polymer was sulfonated in the same manner as in Example 1 to obtain 180.5 g of a sulfonated polymer. An IR spectrum thereof is shown in FIG. 2.

EXAMPLE 3

Reaction was conducted in-the same manner as in Example 1, except that the amounts of the feed monomers, i.e., 2,5-dichloro-4'-phenoxybenzophenone and 3,4'-bis(4-chlorobenzoylamino)diphenyl ether, were changed to 150.50 g (420 mmol) and 85.91 g (180 mmol), respectively. As a result, a polymer was obtained in an amount of 184.1 g. It had a weight-average molecular weight of 145,200.

Figure 3:
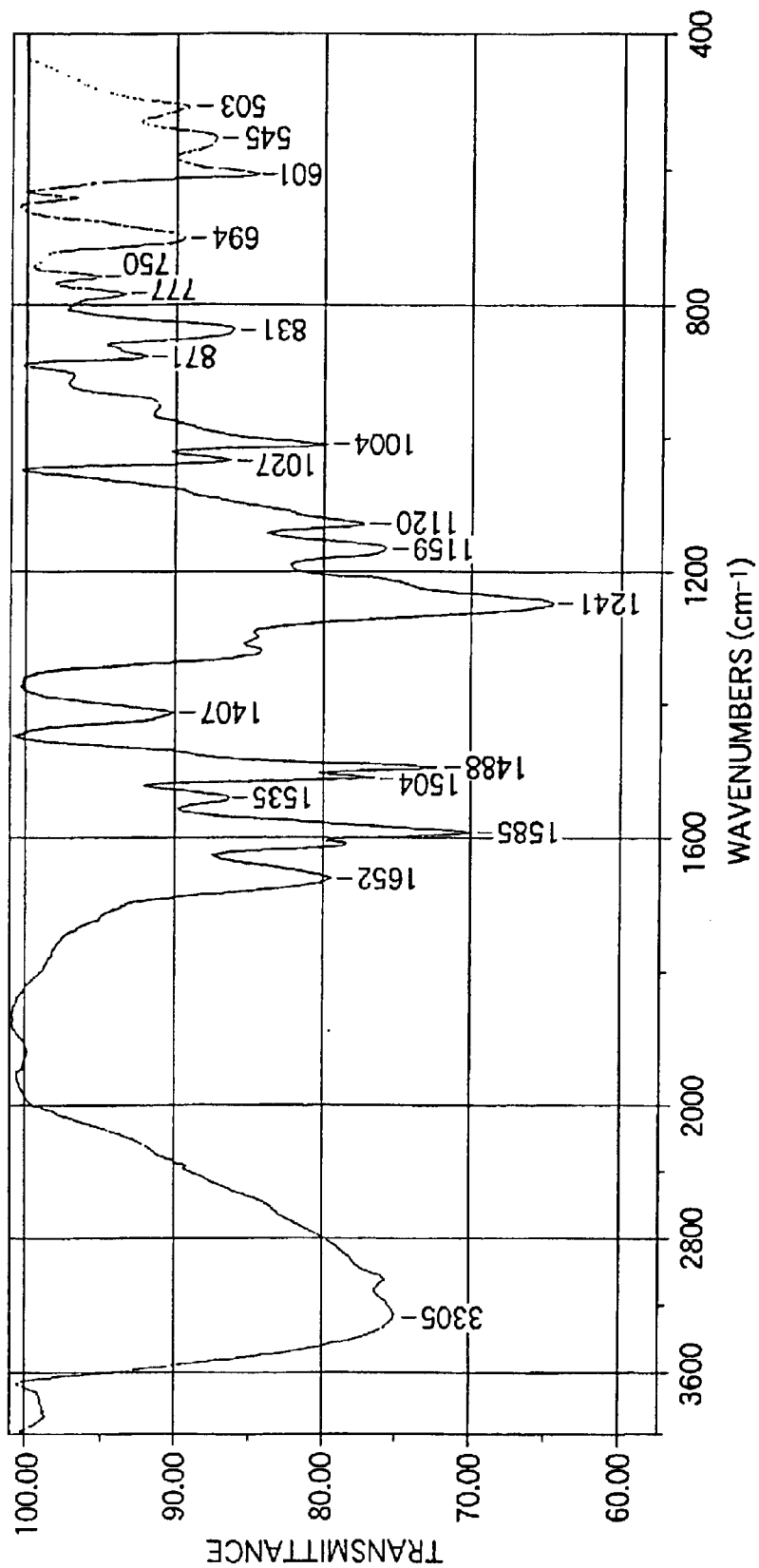
FIG. 3 is an IR chart of the sulfonated polymer obtained in Example 3.

A 150 g portion of the polymer was sulfonated in the same manner as in Example 1 to obtain 176.2 g of a sulfonated polymer. An IR spectrum thereof is shown in FIG. 3.

EXAMPLE 4

Figure 4:
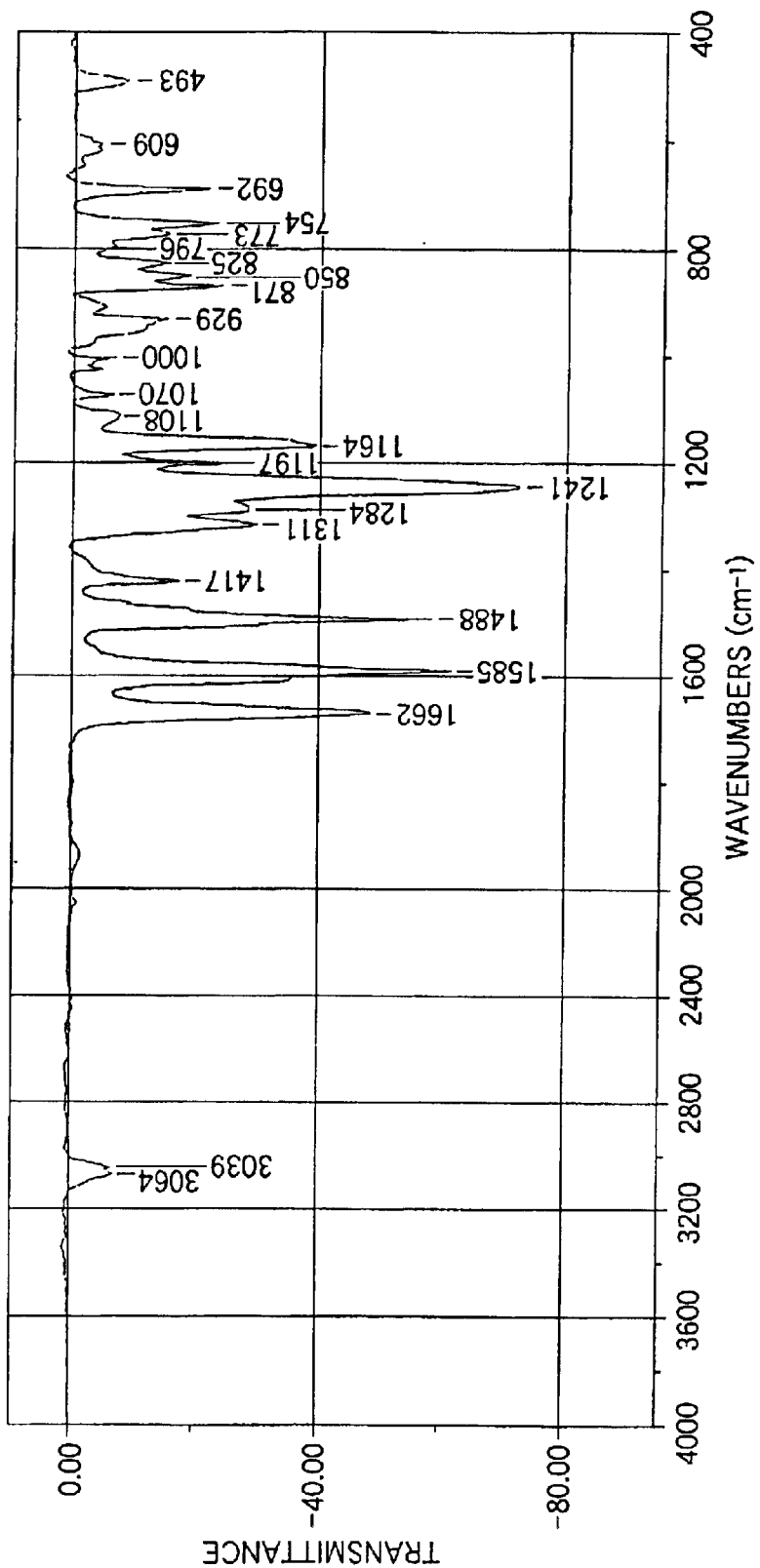
FIG. 4 is an IR chart of the polyarylene copolymer obtained in Example 4.

Reaction was conducted in the same manner as in Example 1, except that 26.84 g (60 mmol) of 4,4'-bis(4-chlorobenzoyl)diphenyl ether was used in place of 28.64 g (60 mmol) of 3,4'-bis(4-chlorobenzoylamino)diphenyl ether. As a result, a polymer was obtained in an amount of 168.9 g. It had a weight-average molecular weight of 135,400. An IR spectrum of the polyarylene copolymer obtained is shown in FIG. 4.

Figure 5:
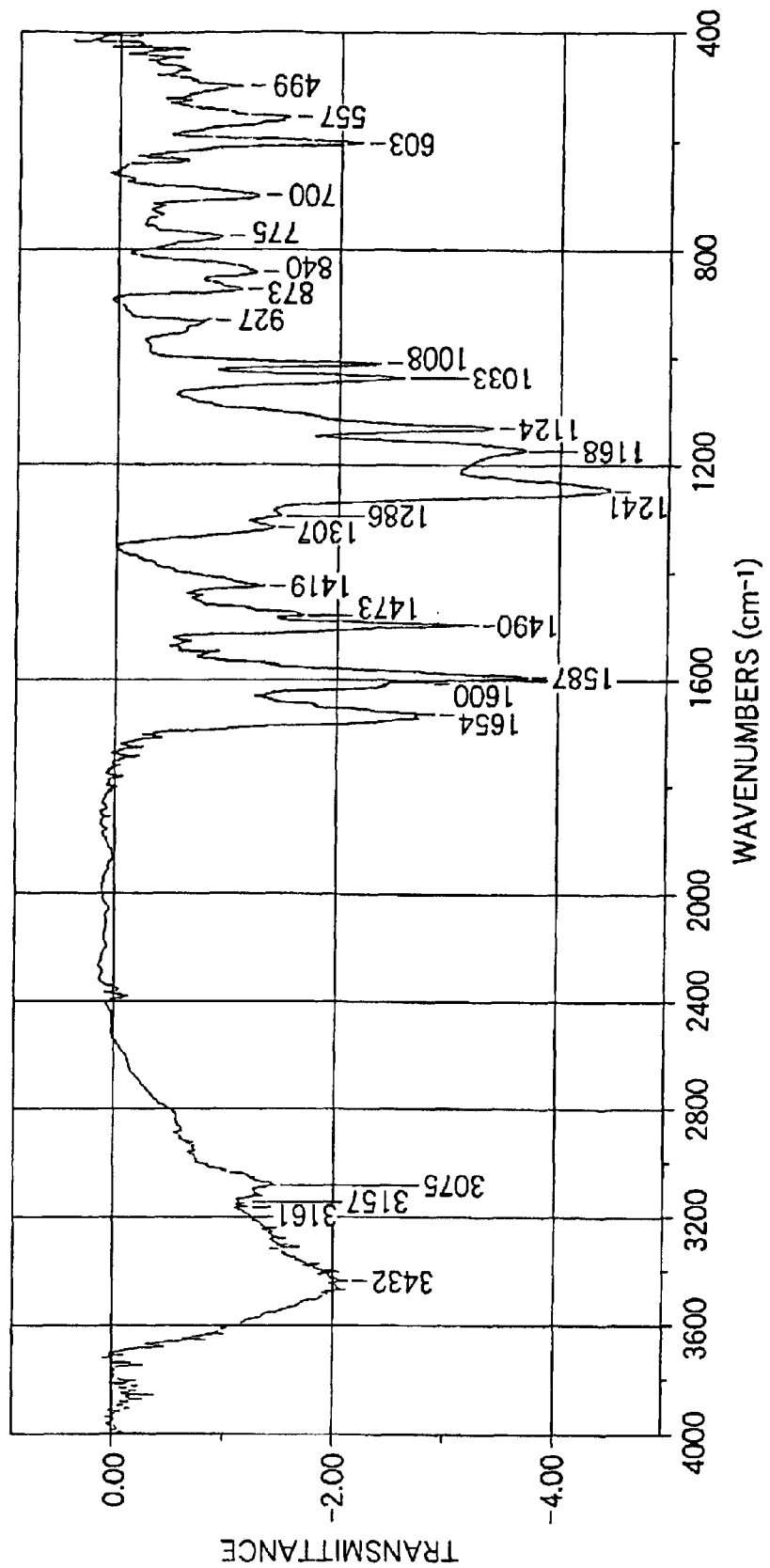
FIG. 5 is an IR chart of the sulfonated polymer obtained in Example 5.

A 150 g portion of the polymer was sulfonated in the same manner as in Example 1 to obtain 188.6 g of a sulfonated polymer. An IR spectrum thereof is shown in FIG. 5.

EXAMPLE 5

Reaction was conducted in the same manner as in Example 1, except that the amount of 2,5-dichloro-4'-phenoxybenzene was changed to 188.04 g (525 mmol) and the amount of 3,4'-bis(4-chlorobenzoylamino)diphenyl ether was changed to 33.55 g (75 mmol). As a result, a polymer was obtained in an amount of 170.0 g. It had a weight-average molecular weight of 138,200.

A 150 g portion of the polymer was sulfonated in the same manner as in Example 1 to obtain 187.5 g of a sulfonated polymer.

COMPARATIVE EXAMPLE 1

Polymerization reaction was conducted in the same manner as in Example 1, except that 214.9 g (600 mmol) of 2,5-dichloro-4'-phenoxybenzophenone was used as the only monomer. As a result, a polymer was obtained in an amount of 161 g. This polymer had a weight-average molecular weight of 192,800. It swelled considerably in methanol.

A 150 g portion of the polymer was sulfonated in the same manner as in Example 1 to obtain 190.2 g of a sulfonated polymer.

COMPARATIVE EXAMPLE 2

Reaction was conducted in the same manner as in Example 1, except that the amounts of 2,5-dichloro-4'-phenoxybenzophenone and 3,4'-bis(4-chlorobenzoylamino) diphenyl ether were changed to 210.70 g (588 mmol) and 5.72 g (12 mmol), respectively. As a result, a polymer was obtained in an amount of 165.1 g. It had a weight-average molecular weight of 158,800.

A 150 g portion of the polymer was sulfonated in the same manner as in Example 1 to obtain 188.6 g of a sulfonated polymer.

The polymers obtained in Examples 1 to 5 and Comparative Examples 1 and 2 were dissolved in NMP in a concentration of 10%. The resultant solutions each was cast on a glass plate and dried at 100° C. finally in a vacuum to remove the solvent. Thus, membranes were produced. Properties of the polymers obtained are summarized in Table 1.

TABLE 1

|  | Equivalent Weight for Sulfonic acid (meq/g) | Proton conductivity (S/cm) | Tensile strength (kg/cm$^2$) | Behavior in hot water |
| --- | --- | --- | --- | --- |
| Example 1 | 2.47 | 2.67 × 10$^{-3}$ | 686 | ○ |
| Example 2 | 2.36 | 2.55 × 10$^{-3}$ | 745 | ○ |
| Example 3 | 2.12 | 2.44 × 10$^{-3}$ | 980 | ○ |
| Example 4 | 2.39 | 2.34 × 10$^{-3}$ | 920 | ○ |
| Example 5 | 2.23 | 2.35 × 10$^{-3}$ | 845 | ○ |
| Comparative Example 1 | 2.97 | 2.16 × 10$^{-3}$ | 320 | X |
| Comparative Example 2 | 3.03 | 2.27 × 10$^{-3}$ | 345 | X |

EXAMPLE 6

Figure 6:
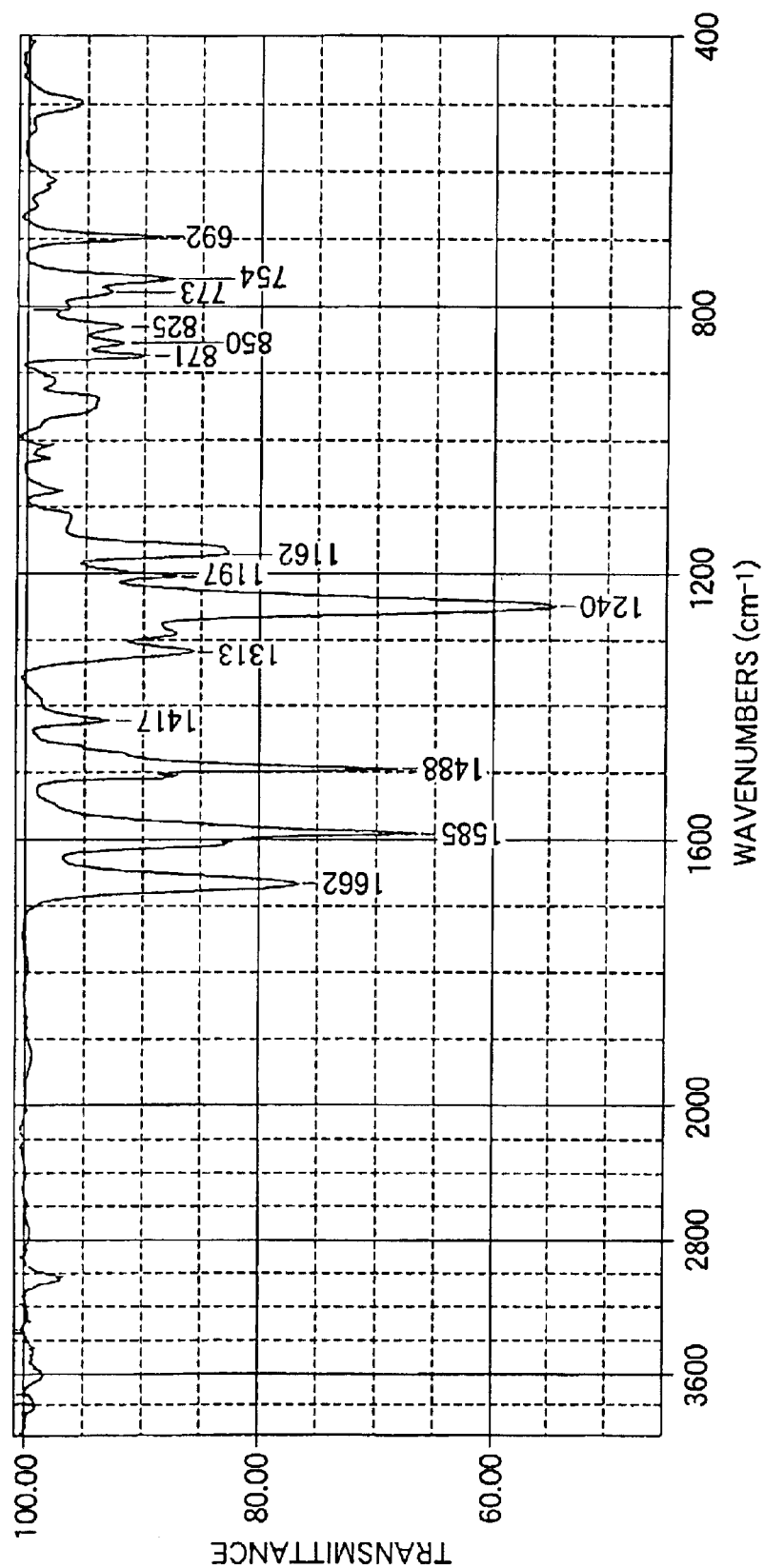
FIG. 6 is an IR chart of the polyarylene obtained in Example 6.

Into a three-necked flask equipped with a ball condenser and a three-way cock were introduced 193.5 g (540 mmol) of 2,5-dichloro-4'-phenoxybenzophenone, 15.1 g (60 mmol) of 4,4'-dichlorobenzophenone, 11.7 g (78 mmol) of sodium iodide, 11.8 g (18 mmol) of bis(triphenylphosphine)nickel dichloride, 63.0 g (240 mmol) of triphenylphosphine, and 94.1 g (1.44 mol) of zinc. This flask was placed on a 70° C. oil bath and the atmosphere in the flask was replaced with nitrogen. Thereafter, 1,000 ml of N-methyl-2-pyrrolidone was added to the mixture in a nitrogen atmosphere to initiate a reaction. The reaction mixture was reacted for 20 hours and then diluted with 500 ml of N-methyl-2-pyrrolidone. The resultant reaction mixture which had undergone polymerization was poured into a 1:10 mixture of hydrochloric acid and methanol to precipitate a polymer. The precipitate was washed, recovered by filtration, and then dried in vacuo. Thus, a white powder was obtained in an amount of 153 g. This polymer had a weight-average molecular weight of 159,000. The polymer obtained was formed into membrane using N-methyl-2-pyrrolidone as a casting solvent. This membrane was immersed in methanol, but no swelling was observed. An IR spectrum of the polymer obtained in shown in FIG. 6.

Figure 7:
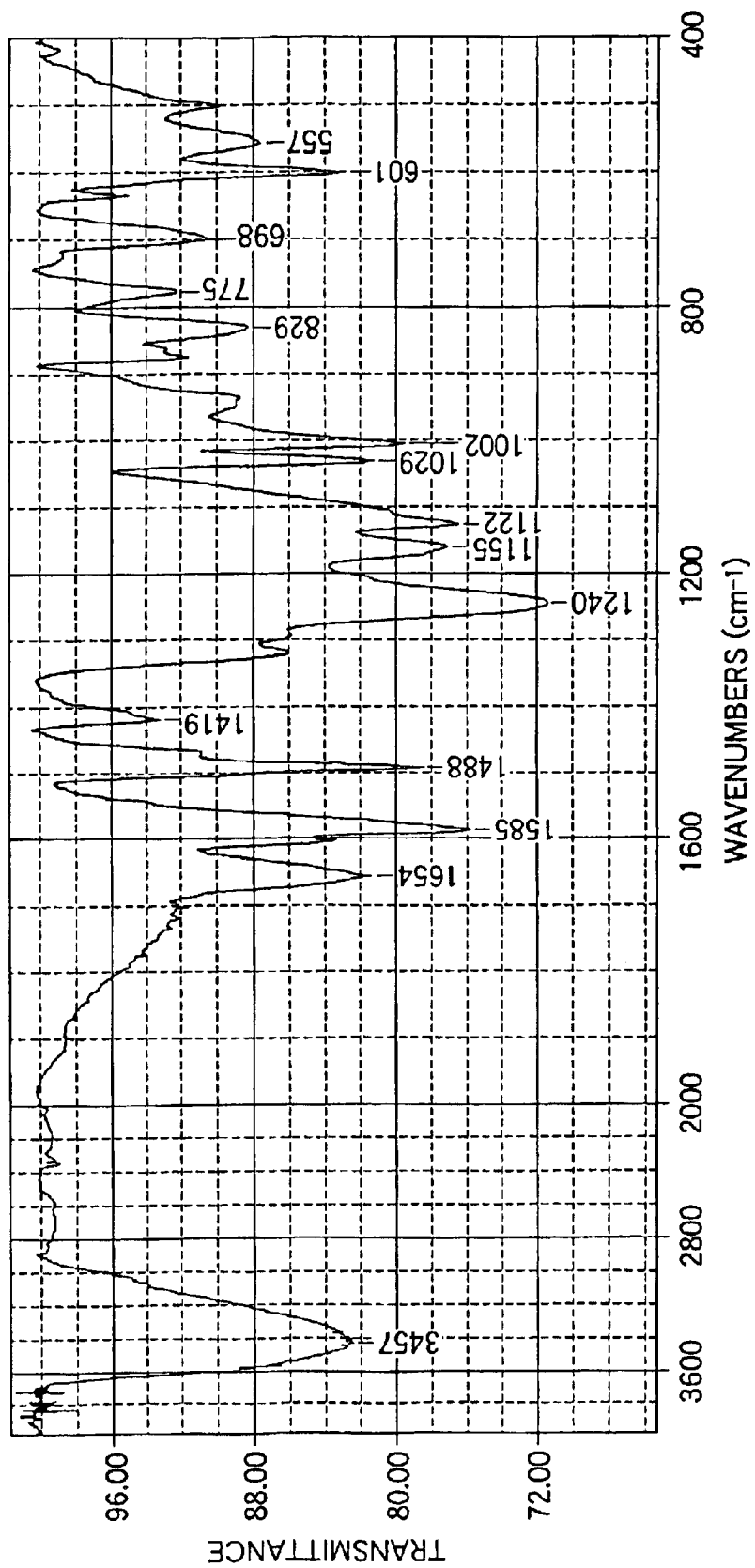
FIG. 7 is an IR chart of the sulfonated polymer obtained in Example 6.

To 150 g of the polymer obtained above was added 1,500 ml of concentrated sulfuric acid. This mixture was stirred at room temperature for 24 hours to sulfonatation. After the reaction, the reaction mixture was poured into a large amount of pure water to precipitate the sulfonated polymer. The resulting polymer was washed with water until the washing water came to near neutral pint. Thereafter, the sulfonated polymer was recovered by filtration and dried at 90° C. in vacuo. 179 g of the sulfonated polymer was thus yielded. An IR spectrum thereof is shown in FIG. 7.

EXAMPLE 7

Reaction was conducted in the same manner as in Example 6, except that the amounts of 2,5-dichloro-4'-phenoxybenzophenone and 4,4'-dichlorobenzophenone were changed to 182.7 g (510 mmol) and 22.6 g (90 mmol), respectively. As a result, a polymer was obtained in an amount of 150 g. It had a weight-average molecular weight of 143,500.

Sulfonation was conducted in the same manner as in Example 6 to obtain 175 g of a sulfonated polymer.

EXAMPLE 8

Figure 8:
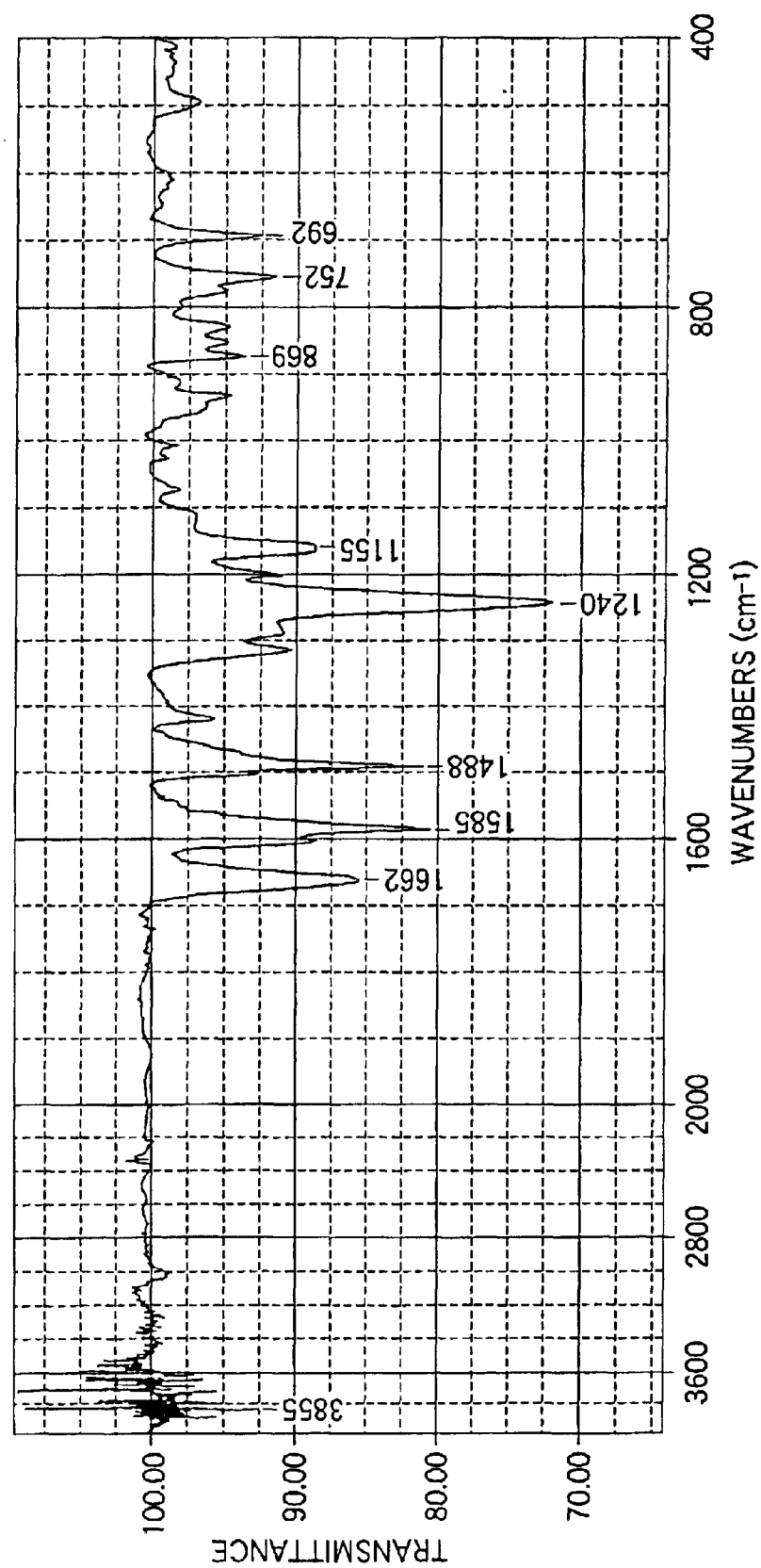
FIG. 8 is an IR chart of the polyarylene obtained in Example 8.

Reaction was conducted in the same manner as in Example 6, except that the amounts of 2,5-dichloro-4'- phenoxybenzophenone and 4,4'-dichlorobenzophenone were changed to 171.6 g (480 mmol) and 30.13 g (120 mmol), respectively. As a result, a polymer was obtained in an amount of 148 g. It had a weight-average molecular weight of 129,600. An IR spectrum of the polymer obtained is shown in FIG. 8.

Sulfonation was conducted in the same manner as in Example 6 to obtain 171 g of a sulfonated polymer.

Figure 9:
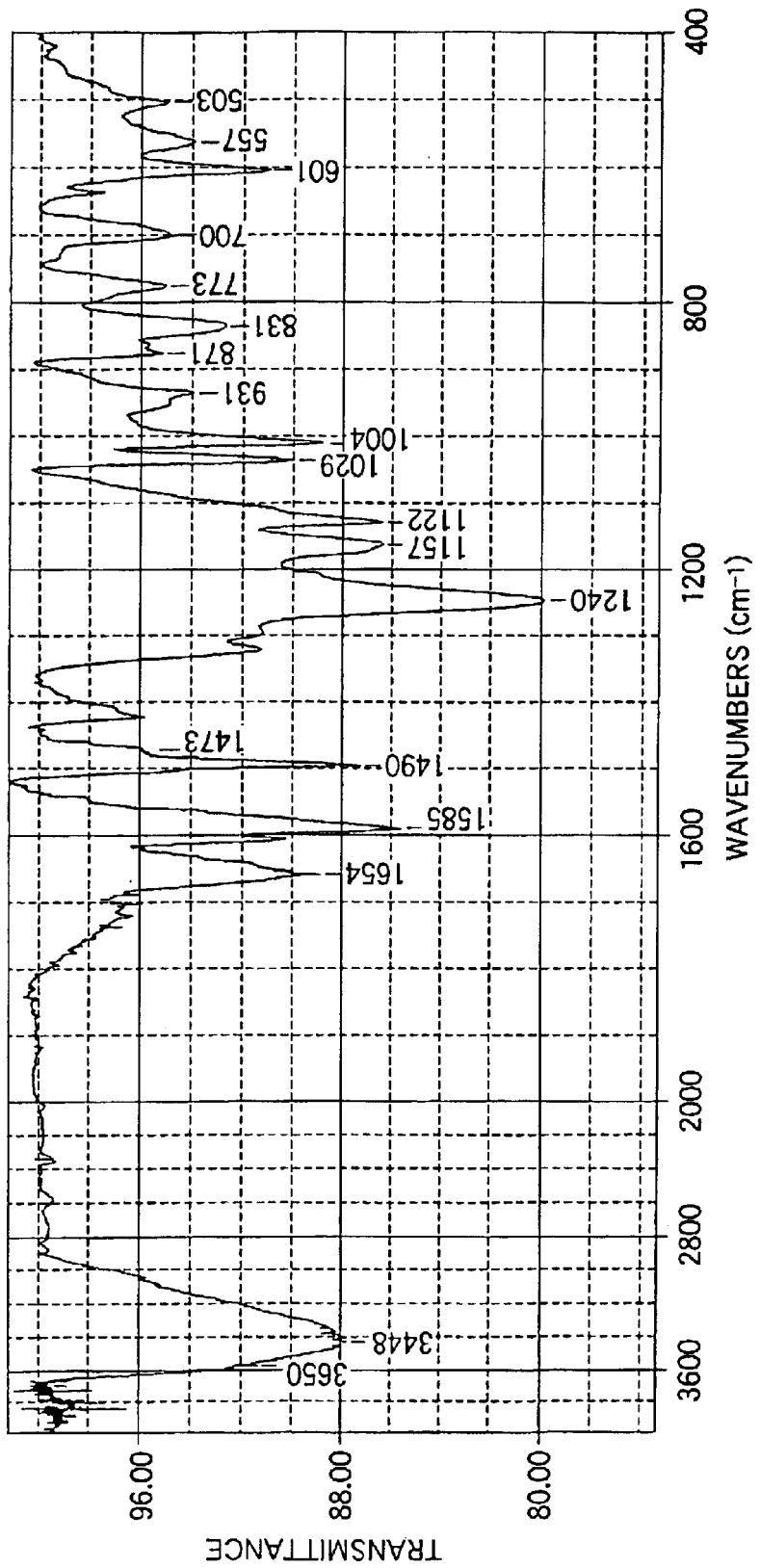
FIG. 9 is an IR chart of the sulfonated polymer obtained in Example 8.

An IR spectrum of the sulfonated polymer is shown in FIG. 9.

EXAMPLE 9

Reaction was conducted in the same manner as in Example 6, except that the amounts of 2,5-dichloro-4'-phenoxybenzophenone and 4,4'-dichlorobenzophenone were changed to 154.0 g (420 mmol) and 45.2 g (180 mmol), respectively. As a result, a polymer was obtained in an amount of 142 g. It had a weight-average molecular weight of 63,800.

Sulfonation was conducted in the same manner as in Example 6 to obtain 162 g of a sulfonated polymer.

The polymers obtained in Examples 6 to 9 were dissolved in NMP in a concentration of 10%. The resultant solutions each was cast on a glass plate and dried at 100° C. finally in a vacuum to remove the solvent. Thus, membranes were produced. Properties of the polymers obtained are summarized in Table 2.

TABLE 2

| | Poly(4,4'-benzophenone) chain in copolymer (mol %) | Equivalent weight of sulfonic acid (meq/g) | Proton conductivity (S/cm) | Tensile strength (kg/cm$^2$) | Behavior in hot water |
|---|---|---|---|---|---|
| Example 6 | 10 | 2.59 | 2.56 × 10$^{-3}$ | 560 | ○ |
| Example 7 | 15 | 2.48 | 2.36 × 10$^{-3}$ | 575 | ○ |
| Example 8 | 20 | 2.33 | 2.10 × 10$^{-3}$ | 623 | ○ |
| Example 9 | 30 | 2.25 | 1.98 × 10$^{-3}$ | 750 | ○ |

EXAMPLE 10

Polymerization reaction was conducted under the same conditions as in Example 6, except that 29.5 g (60 mmol) of bis(4-trifluoromethylsulfonyloxyphenyl)hexafluoropropane was used in place of 15.1 g (60 mmol) of 4,4'-dichlorobenzophenone.

Figure 10:
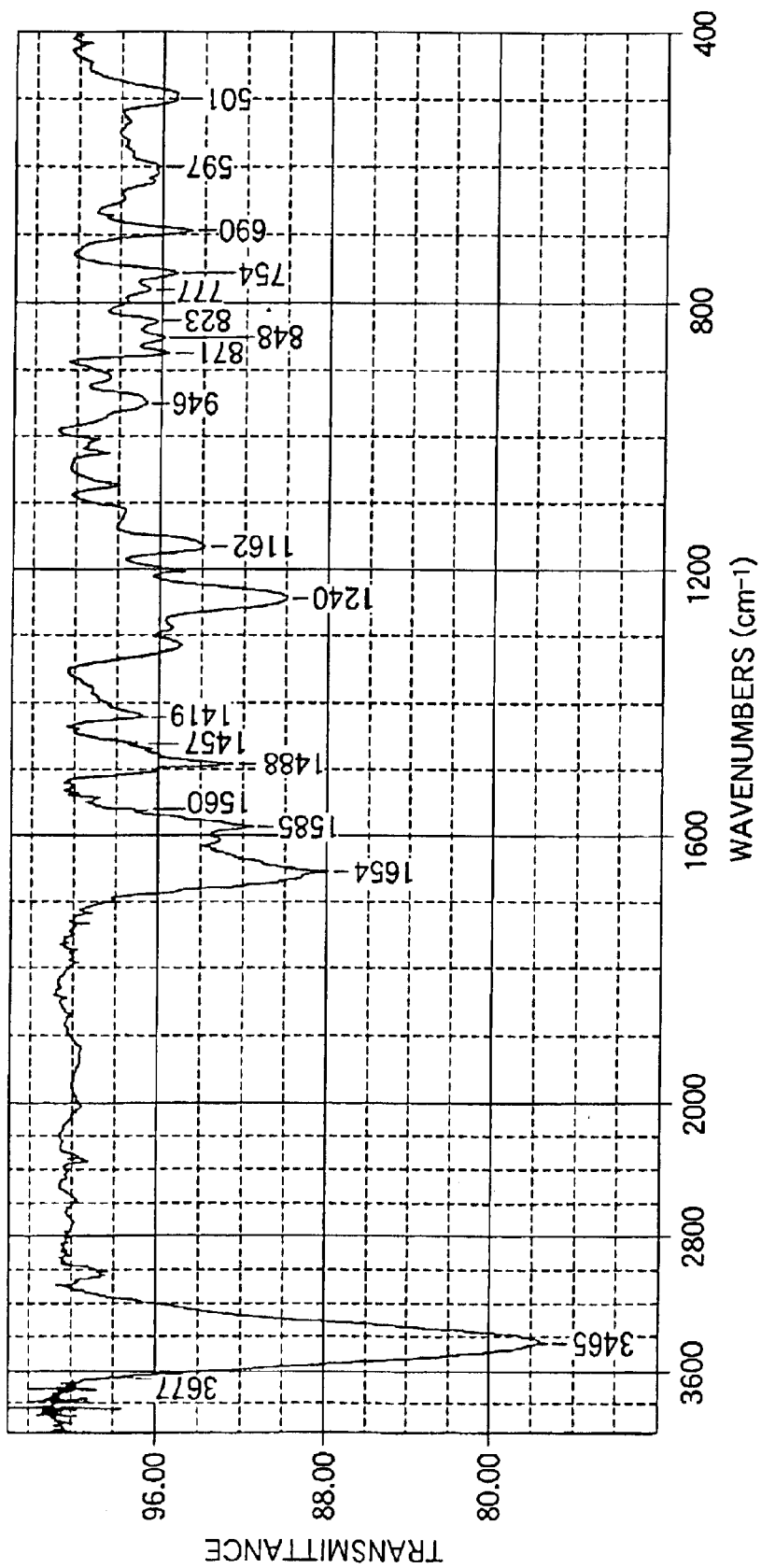
FIG. 10 is an IR chart of the polyarylene obtained in Example 10.

Thus, a polymer was obtained in an amount of 165 g. It had a weight-average molecular weight of 294,000. An IR spectrum of the polymer obtained is shown in FIG. 10.

Sulfonation was conducted in the same manner as in Example 6 to obtain 196 g of a sulfonated polymer.

Figure 11:
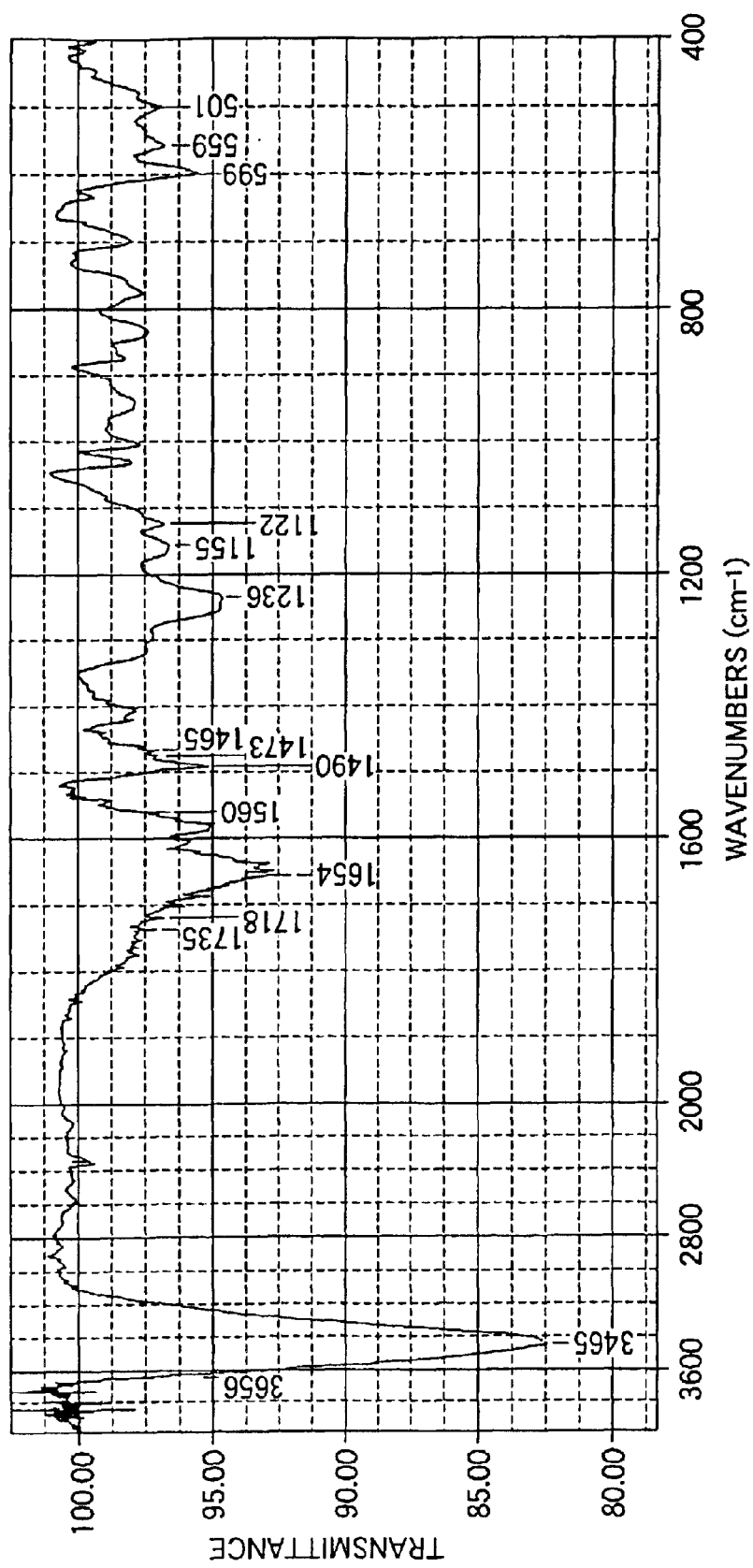
FIG. 11 is an IR chart of the sulfonated polymer obtained in Example 10.

An IR spectrum of the sulfonated polymer is shown in FIG. 11.

EXAMPLE 11

Polymerization reaction was conducted under the same conditions as in Example 9, except that 88.6 g (180 mmol) of bis(4-trifluoromethylsulfonyloxyphenyl)hexafluoropropane was used in place of 45.2 g (180 mmol) of 4,4'-dichlorobenzophenone.

Figure 12:
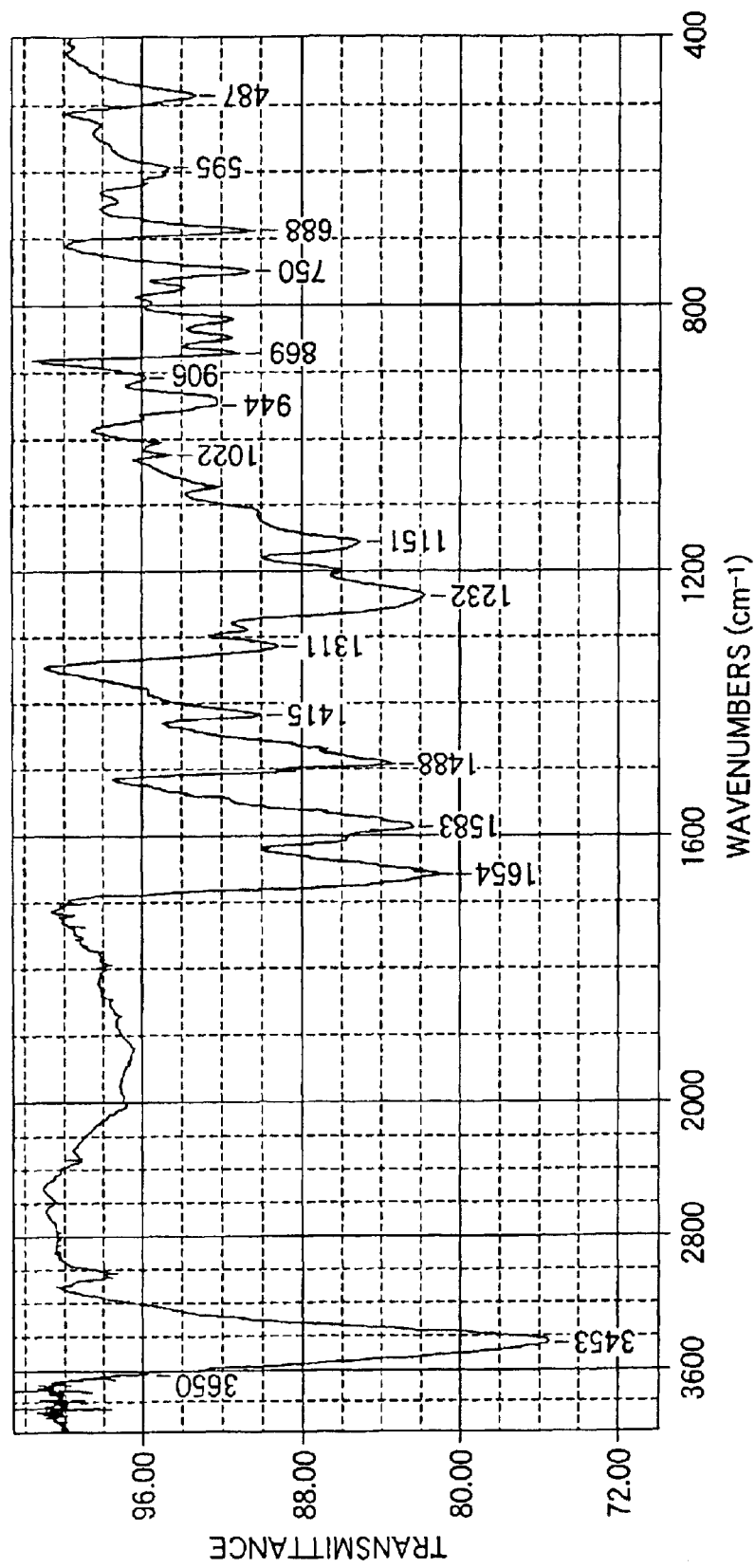
FIG. 12 is an IR chart of the polyarylene obtained in Example 11.

Thus, a polymer was obtained in an amount of 166 g. It had a weight-average molecular weight of 116,000. An IR spectrum of the polymer obtained is shown in FIG. 12.

Sulfonation was conducted in the same manner as in Example 6 to obtain 180 g of a sulfonated polymer.

Figure 13:
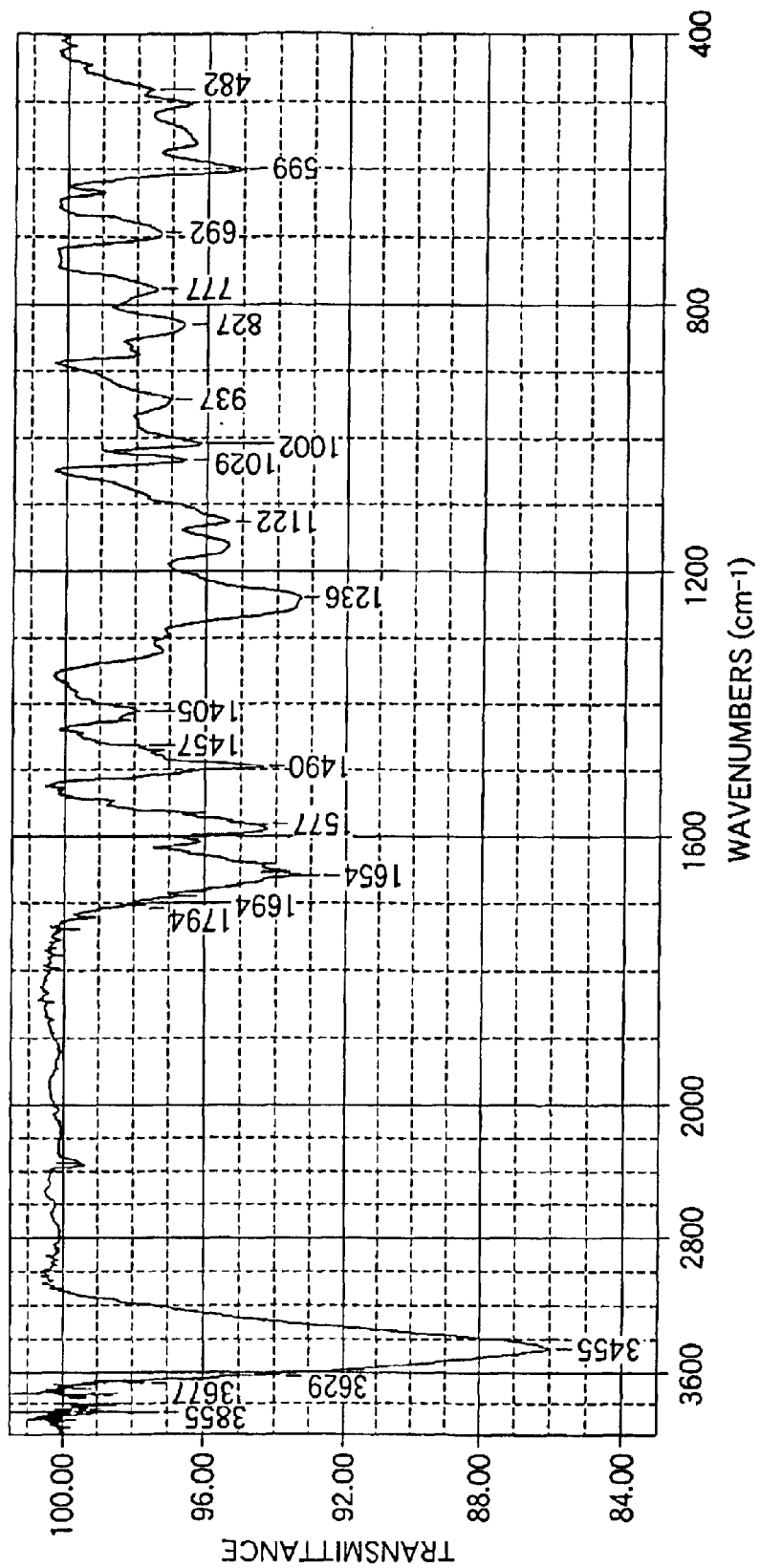
FIG. 13 is an IR chart of the sulfonated polymer obtained in Example 11.

An IR spectrum of the sulfonated polymer is shown in FIG. 13.

The polymers obtained in Examples 10 and 11 were dissolved in NMP in a concentration of 10%. The resulting solutions each was cast on a glass plate and dried at 100° C. finally in a vacuum to remove the solvent. Thus, membranes were produced. Properties of the polymers obtained are summarized in Table 3.

TABLE 3

| Example No. | 4,4'-Diphenyl-hexafluoro-propane chain in copolymer (mol %) | Equivalent weight of sulfonic acid (meq/g) | Proton conductivity (S/cm) | Tensile strength (kg/cm$^2$) | Behavior in hot water |
|---|---|---|---|---|---|
| 10 | 10 | 2.42 | 2.41 × 10$^{-3}$ | 520 | ○ |
| 11 | 30 | 2.15 | 2.25 × 10$^{-3}$ | 575 | ○ |

EXAMPLE 12

Polymerization and post-treatment were conducted in the same manners as in Example 6, except that 1.29 g (6 mmol) of 4-chlorobenzophenone was used as a molecular weight modifier in addition to the monomers of 193.5 g (540 mmol) of 2,5-dichloro-4'-phenoxybenzophenone and 15.1 g (60 mmol) of 4,4'-dichloro-benzophenone.

Thus, a copolymer was obtained in an amount of 159 g. It had a weight-average molecular weight of 130,800.

Using 150 g of the polymer, sulfonation was conducted in the same manner as in Example 6, and post-treatment, drying and membrane formation were also conducted in the same manners as in Example 6. Because the viscosity was low as compared with the solution viscosity of the polymerized and sulfonated polymer to which the molecular weight modifier was not added, a membrane having smooth and good surface was formed.

EXAMPLE 13

Polymerization and post-treatment were conducted in the same manners as in Example 12, except that 2.58 g (12 mmol) of 4-chlorobenzophenone was used in place of 1.29 g (6 mmol) of 4-chlorobenzophenone.

Thus, a copolymer having controlled molecular weight was obtained in an amount of 159 g. It had a weight-average molecular weight of 94,600.

Using 150 g of the polymer, sulfonation was conducted in the same manner as in Example 6, and post-treatment, drying and membrane formation were also conducted in the same manners as in Example 6. Because the viscosity was low as compared with the solution viscosity of the polymerized and sulfonated polymer to which the molecular weight modifier was not added, a membrane having smooth and good surface was formed.

TABLE 4

| Example | 4-Chloro-benzophenone (mol %) | Weight average molecular weight | Equivalent weight of sulfonic acid (meq/g) | Proton conductivity (S/cm) | Tensile strength (kg/cm$^2$) | Behavior in hot water |
|---|---|---|---|---|---|---|
| Example 12 | 1 | 130,800 | 2.55 | 2.56 | 575 | ○ |
| Example 13 | 2 | 94,600 | 2.578 | 2.62 | 560 | ○ |

The polyarylene copolymers of the invention can be sulfonated while easily regulating the amount of sulfonic acid groups to be incorporated. The sulfonic acid-containing polyarylene copolymers obtained are useful as a conductive membrane having high proton conductivity in a wide temperature range. The sulfonated polymer shows excellent adhesion to substrates and electrodes, is not brittle, and has excellent strength and excellent resistance to hot water.

Consequently, the sulfonated polymers of the invention are utilizable as a conductive membrane in applications such as electrolytes for primary batteries, electrolytes for secondary batteries, solid polymer electrolytes for fuel cells, display elements, various sensors, signal-transmitting media, solid capacitors, and ion-exchange membranes. Therefore, the invention is of great industrial significance.

What is claimed is:

1. A proton-conductive membrane comprising a polyarylene copolymer having sulfonic acid groups, the polyarylene copolymer comprising (A) aromatic compound units having a main chain containing one or more electron-withdrawing groups therein and (B) aromatic compound units having a main chain containing no electron-withdrawing groups therein.

2. The proton-conductive membrane of claim 1, wherein the polyarylene copolymer comprises (A) 60 mol % or less than 60 mol % aromatic compound units having a main chain containing one or more electron-withdrawing groups therein and (B) 40 mol % or more less than 40 mol % aromatic compound units having a main chain containing no electron-withdrawing groups therein (provided that (A)+(B)=100 mol %, and (A) is not 0 mol %).

3. The proton-conductive membrane of claim 1, wherein the polyarylene copolymer comprises (A) from 60 to 0.01 mol % aromatic compound units having a main chain containing one or more electron-withdrawing groups therein and (B) from 40 to 99.99 mol % aromatic compound units having a main chain containing no electron-withdrawing groups therein (provided that (A)+(B)=100 mol %).

4. The proton-conductive membrane of claim 1, wherein the aromatic compound units (A) having a main chain containing one or more electron-withdrawing groups therein are structures represented by the following general formula (1):

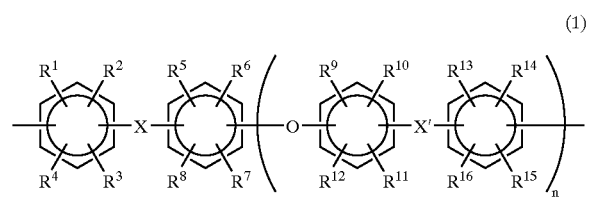

(1)

wherein X and X' each represents at least one divalent electron-withdrawing group selected from the group consisting of —CO—, —CONH—, —(CF$_2$)$_p$— (wherein p is an integer of 1 to 10), —C(CF$_3$)$_2$—, —COO—, —SO— and —SO$_2$—; R$^1$ to R$^{16}$ may be the same or different and each represents a hydrogen atom, a halogen atom, an alkyl group, a halogenoalkyl group, an allyl group, or an aryl group; and n is a number of 0 or 1.

5. The proton-conductive membrane of claim 1, wherein the aromatic compound units (B) having a main chain containing no electron-attracting groups therein are structures represented by at least one of the following general formulae (2) to (4):

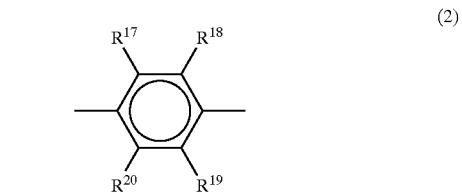

(2)

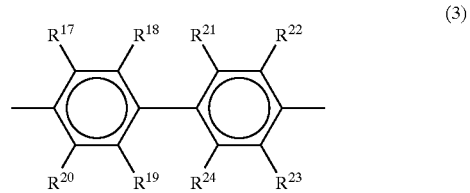

(3)

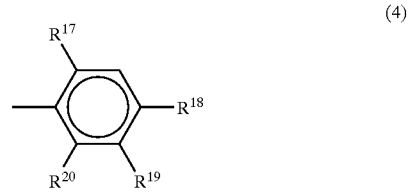

(4)

wherein R$^{17}$ to R$^{24}$ may be the same or different and each represents a hydrogen atom, an alkyl group, a halogen atom, a halogenoalkyl group, an aryl group, or a group represented by the formula

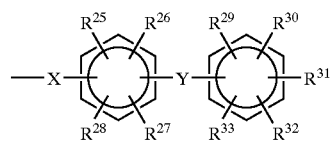

wherein X represents an electron-attracting divalent group; Y represents an electron-donating divalent group; and R$^{25}$ to R$^{33}$ each represents a hydrogen atom, an alkyl group, a halogen atom, or a halogenoalkyl group.

6. The proton-conductive membrane of claim 1, wherein the polyarylene copolymer comprises from 35 to 7 mol% structural units derived from 4,4'-benzophenone as the aromatic compound units (A) having a main chain containing one or more electron-withdrawing groups therein and from 65 to 93 mol % structural units derived from 4'-phenoxy-2,5-benzophenone as the aromatic compound units (B) having a main chain containing no electron-withdrawing groups therein and which has sulfonic acid groups in an amount of from 2.0 to 3.5 meq per g of the polymer.

7. The proton-conductive membrane of claim 1, wherein the polyarylene copolymer comprises from 40 to 3 mol % structural units derived from 4,4'-bis(benzoyl)diphenyl ether as the aromatic compound units (A) having a main chain containing one or more electron-withdrawing groups therein and from 60 to 97 mol % structural units derived from 4'-phenoxy-2,5-benzophenone as the aromatic compound units (B) having a main chain containing no electron-withdrawing groups therein (provided that (A)+(B)=100 mol %) and which has sulfonic acid groups in an amount of from 1.5 to 3.5 meq per g of the polymer.

8. The proton-conductive membrane of claim 1, wherein the sulfonic acid groups are present in an amount of from 1 to 5 meq per gram of the polyarylene copolymer.

9. The proton-conductive membrane of claim 1, wherein the number of the sulfonic acid groups is from 0.05 to 2 per unit (B) as a component of the polyarylene copolymer.

10. Polyarylene copolymer having sulfonic acid groups, comprising (A) from 60 to 0.01 mol % aromatic compound units having a main chain containing one or more electron-withdrawing groups therein and (B) from 40 to 99.99 mol % aromatic compound units having a main chain containing no electron-withdrawing groups therein (provided that (A)+(B)=100 mol %).

11. The polyarylene copolymer of claim 10, wherein the aromatic compound units (A) having a main chain containing one or more electron-withdrawing groups therein are structures represented by the following general formula (1):

(1)

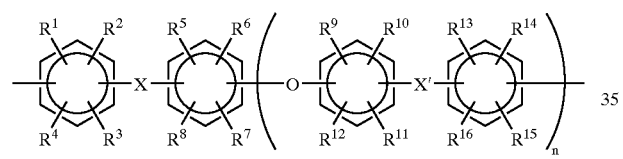

wherein X and X' each represents at least one divalent electron-withdrawing group selected from the group consisting of —CO—, —CONH—, —(CF$_2$)$_p$— (wherein p is an integer of 1 to 10), —C(CF$_3$)$_2$—, —COO—, —SO— and —SO$_2$—; R$^1$ to R$^{16}$ may be the same or different and each represents a hydrogen atom, a halogen atom, an alkyl group, a halogenoalkyl group, an allyl group, or an aryl group; and n is a number of 0 or 1.

12. The polyarylene copolymer of claim 1, wherein the aromatic compound units (B) having a main chain containing no electron-attracting groups therein are structures represented by at least one of the following general formulae (2) to (4):

(2)

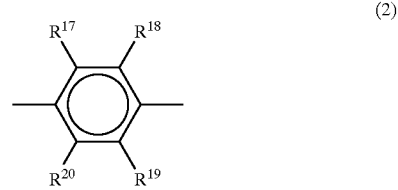

(3)

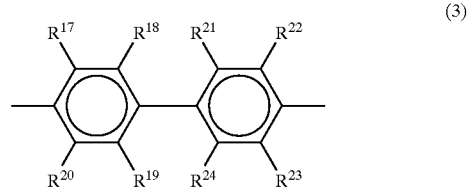

(4)

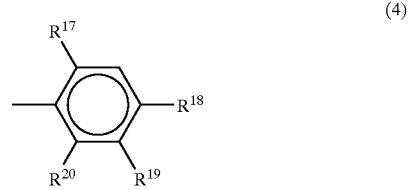

wherein R$^{17}$ to R$^{24}$ may be the same or different and each represents a hydrogen atom, an alkyl group, a halogen atom, a halogenoalkyl group, an aryl group, or a group represented by the formula

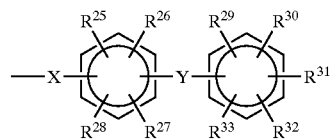

wherein X represents an electron-attracting divalent group; Y represents an electron-donating divalent group; and R$^{25}$ to R$^{33}$ each represents a hydrogen atom, an alkyl group, a halogen atom, or a halogenoalkyl group.

* * * * *